(12) United States Patent
Takayama et al.

(10) Patent No.: US 6,556,606 B2
(45) Date of Patent: Apr. 29, 2003

(54) HIGH-POWERED SEMICONDUCTOR LASER ARRAY APPARATUS IN WHICH THE WAVELENGTH AND PHASE OF LASER BEAMS FROM SEMICONDUCTOR LASER UNITS ABOVE CAN BE MATCHED THOSE OF LASER BEAMS FROM SEMICONDUCTOR LASER UNITS BELOW, MANUFACTURING METHOD OF THE SEMICONDUCTOR LASER ARRAY APPARATUS AND MULTI-WAVELENGTH LASER EMITTING APPARATUS USING THE SEMICONDUCTOR LASER ARRAY APPARATUSES

(75) Inventors: Toru Takayama, Nara (JP); Masaaki Yuri, Ibaraki (JP); Seiichiro Tamai, Toyono-gun (JP); Kunio Ito, Uji (JP); Masaru Kazumura, Takatsuki (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 166 days.

(21) Appl. No.: 09/824,470

(22) Filed: Apr. 2, 2001

(65) Prior Publication Data

US 2001/0026573 A1 Oct. 4, 2001

(30) Foreign Application Priority Data

Mar. 31, 2000 (JP) .......................................... 2000-99513
Mar. 31, 2000 (JP) .......................................... 2000-99514

(51) Int. Cl.[7] .............................. H01S 3/19; H01S 3/13

(52) U.S. Cl. ...................... 372/46; 372/18; 372/29.01; 372/50; 257/81

(58) Field of Search ................................ 372/46, 29.07, 372/18, 33, 45, 108; 369/44.37; 257/81

(56) References Cited

U.S. PATENT DOCUMENTS 4,870,651 A * 9/1989 Taneya et al. ................. 372/50
6,233,045 B1 * 5/2001 Suni et al. ..................... 372/33
6,341,118 B1 * 1/2002 Drobot et al. ............ 369/44.37

FOREIGN PATENT DOCUMENTS

JP          359165487 A   *   9/1984

* cited by examiner

Primary Examiner—Albert W. Paladini

(57) ABSTRACT

A semiconductor laser array apparatus, comprising: a first laser array structure which includes a plurality of first laser oscillation units arranged side by side at an interval, and a first current blocking material filling a space between each pair of adjacent laser oscillation units and, a second laser array structure which includes a plurality of second laser array structure arranged side by side at an interval and a second current blocking material filling a space between each pair of adjacent second laser oscillation units. Here, laser beams from the activated first and second laser array structures leak to the outside of those laser array structure so as to form first and second distribution regions of the laser beams respectively, and the first and second laser array structures are close to each other so that the first and second distribution regions contact or overlap with each other.

74 Claims, 14 Drawing Sheets

FIG.3
(1)
(2)
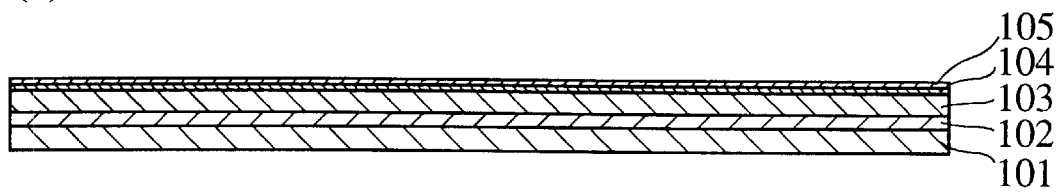
(3)
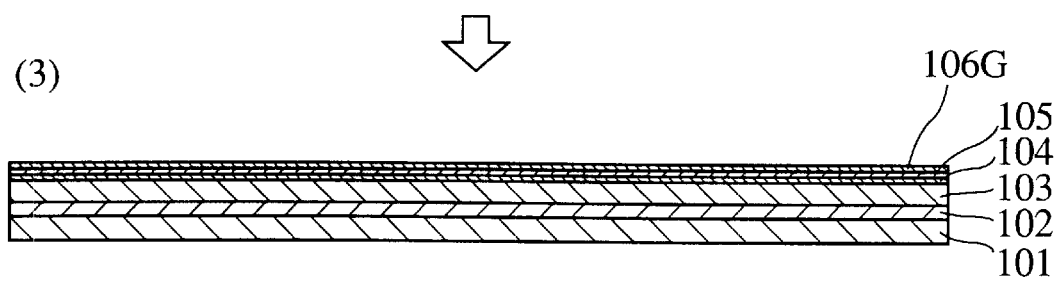
(4)
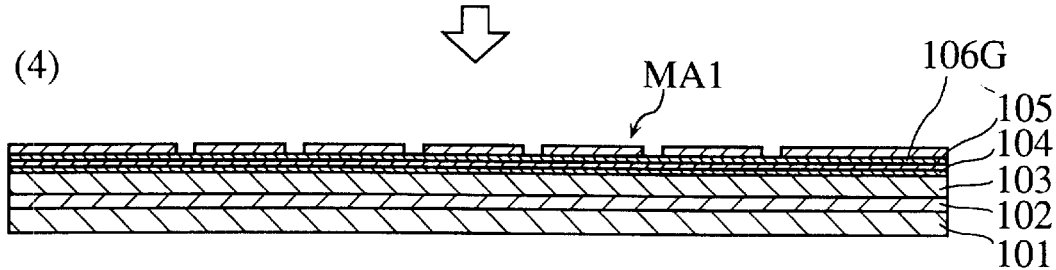
(5)
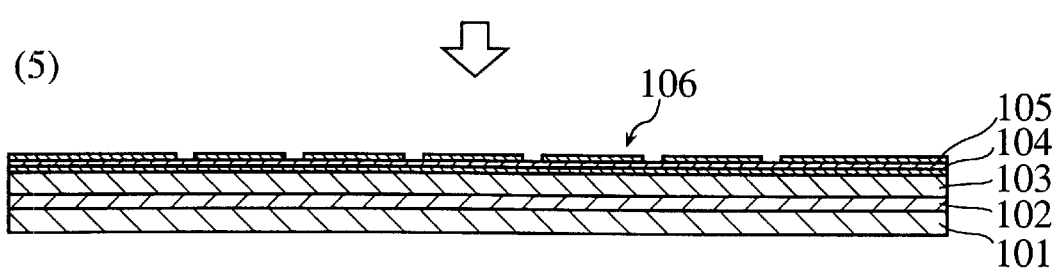

FIG.4
(6)
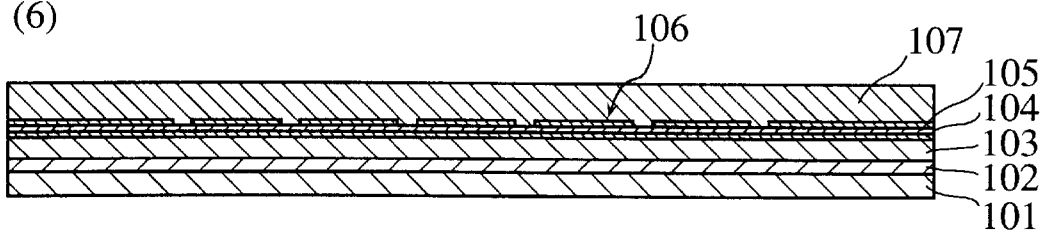
(7)
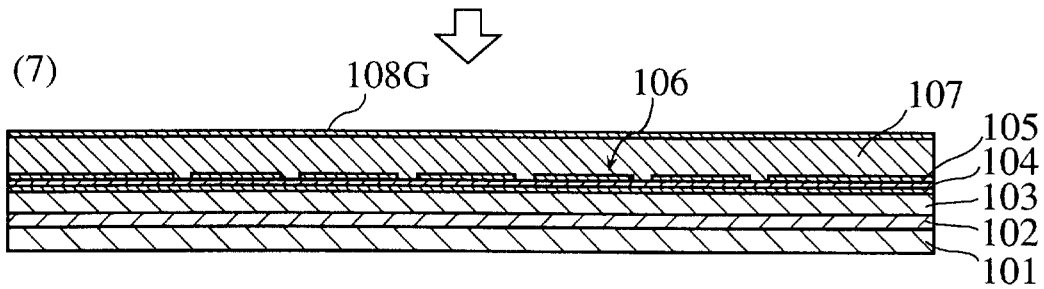
(8)
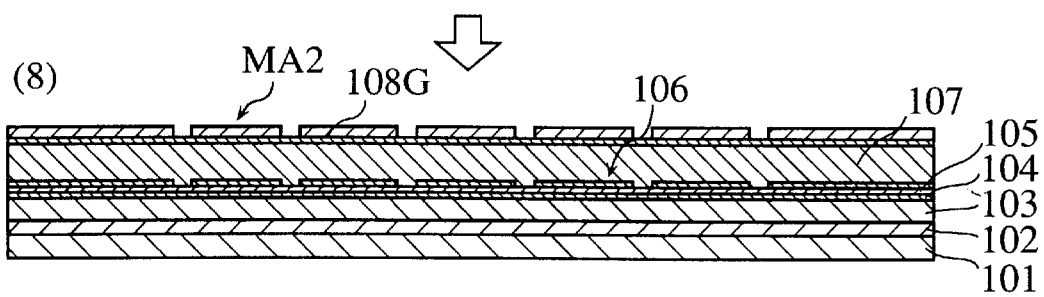
(9)
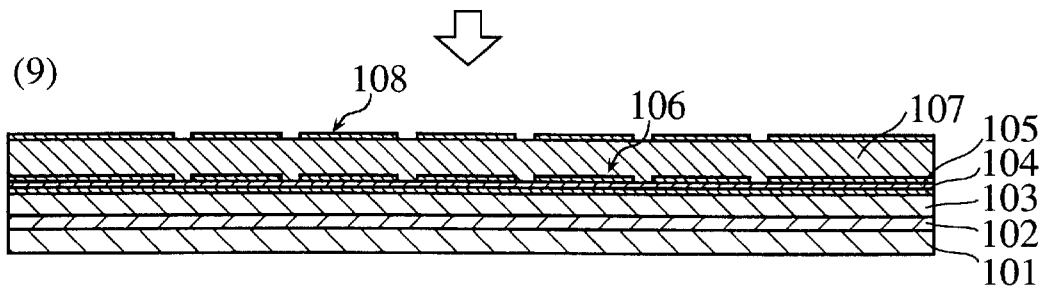

HIGH-POWERED SEMICONDUCTOR LASER ARRAY APPARATUS IN WHICH THE WAVELENGTH AND PHASE OF LASER BEAMS FROM SEMICONDUCTOR LASER UNITS ABOVE CAN BE MATCHED THOSE OF LASER BEAMS FROM SEMICONDUCTOR LASER UNITS BELOW, MANUFACTURING METHOD OF THE SEMICONDUCTOR LASER ARRAY APPARATUS AND MULTI-WAVELENGTH LASER EMITTING APPARATUS USING THE SEMICONDUCTOR LASER ARRAY APPARATUSES

BACKGROUND OF THE INVENTION (1) Field of the Invention

The present invention relates to a high-powered semiconductor laser array apparatus used for optical recording, optical communications, making a hole, welding and the like. The present invention also relates to a manufacturing method for such a semiconductor laser array apparatus, and to a multi-wavelength laser emitting apparatus using such semiconductor laser array apparatuses.

(2) Description of the Related Art

Recently, high-power semiconductor lasers are required for optical recording, optical communications, making an hole, and welding.

In order to meet such a requirement, there is a well-known semiconductor laser apparatus in which a plurality of laser oscillation units are formed in an array structure on the same substrate.

In this apparatus, a high-power light output is obtained by condensing a plurality of laser beams emitted from a plurality of laser oscillation units provided on the same substrate into a spot. Note that in this specification, a laser oscillation unit refers to a portion emitting laser beams and a portion guiding the laser beams.

However, laser beams emitted from those laser oscillation units are different from each other in the wavelength and phase. Therefore, when these laser beams are condensed into a spot, they interfere with each other. As a result, a high-power laser output according to the number of laser oscillation units cannot be obtained.

To cope with the problem, Japanese Laid-Open Patent Application No. H5-226765 discloses a semiconductor laser apparatus. In this apparatus, a plurality of laser oscillation units are placed close to each other on the same substrate so that laser beams from the laser oscillation units interfere with each other at the region of a current blocking layer where laser beams are leaked, whereby the wavelengths and phases of the laser beams can be matched with each other. The laser beams emitted from laser oscillation units are focused into one spot, whereby a high-power semiconductor laser apparatus can be realized.

Meanwhile, when a plurality of array structures are combined, much higher light output power can be expected as compared with only one array structure. However, in the above-stated apparatus, laser beams emitted from the laser oscillation units in the same array structure can be matched with each other in wavelength and phase, but laser oscillation units across different array structures cannot be matched.

Next, some laser emitting apparatuses are applicable for industrial uses such as welding and punching. In these apparatuses, a higher optical power is required. Therefore, gas lasers (such as $CO_2$ lasers and excimer lasers), and solid-state lasers (such as YAG lasers) are currently dominant in this field.

However, a laser emitting apparatus using a gas laser or a solid-state laser inevitably increases in size owing to the structural limitations. Particularly, a laser emitting apparatus using a gas laser needs a gas container within them. Hence, even if a target to be machined is small, an apparatus has to be in a large-scale structure. As a result, a large space is necessary for installing the apparatus, and an expensive apparatus cost is inevitable. In addition, since luminous efficiencies of the gas lasers and solid-state lasers are bad, the apparatus consumes a large amount of electric power. Moreover, in case of gas lasers, their maintenance cost is increased for refilling the gas.

Meanwhile, various workpieces have been developed in accordance with developments of materials. Especially, in case that a workpiece fabricated by mixing two kinds of materials whose laser absorption coefficients are different from each other is processed by the above-stated laser emitting apparatuses, the following problems occur.

The wavelength of laser beam emitted from the above-stated apparatus is fixed at a specific single wavelength, so the wavelength is difficult to be changed. For instance, assuming the workpiece is made of materials A and B, and the material A has a high absorption coefficient for a laser beam with a wavelength $\alpha$, while the material B has a low absorption coefficient for the laser beam, then the laser power has to be increased in order to melt the material B as well. As a result, the temperature of the material A excessively increases, which causes inappropriate parts to be melted. Consequently, in case of making a hole in the above workpiece with these laser apparatuses, a diameter of the hole is larger than the intended dimension and the machining precision deteriorates greatly.

In the above case, it is preferable to also use a laser beam with a wavelength $\beta$. However, it is difficult to change the wavelength of the laser beam in the gas or solid-state multi-wavelength laser emitting apparatus as stated above.

Also in various other fields, there is a demand for a small-sized and high-power laser application equipment with multi-wavelength.

SUMMARY OF THE INVENTION

The first object of the present invention is to provide a semiconductor laser array apparatus in which the above-stated plurality of array structures are combined so that laser beams emitted from the plurality of array structures are matched in wavelength and phase (hereafter called "phase locking"), and a manufacturing method for the same.

The second object of the present invention is to provide a multi-wavelength laser emitting apparatus that realizes a small-sized but relatively high-power laser appliance which emits various laser beams having different wavelengths.

The first object is achieved by a semiconductor laser array apparatus made up of: a first laser array structure which includes, a plurality of first laser oscillation units which are arranged side by side at an interval, and a first current blocking material which fills a space between each pair of adjacent first laser oscillation units; and, a second laser array structure which includes, a plurality of second laser oscillation units which are arranged side by side at an interval, and a second current blocking material which fills a space between each pair of adjacent second laser oscillation units, wherein, when the semiconductor laser array apparatus is activated, laser beams generated by the first laser array structure and the second laser array structure leak to the outside of the first and second laser array structures so as to form first and second distribution regions of the laser beams, and the first and second laser array structures are closely disposed so that the first and second distribution regions contact or overlap with each other.

This construction enables phase locking between the first and second laser array structures. Consequently, in case of condensing laser beams emitted from the laser array structures into one spot, a high light output power can be obtained.

The above construction may include a construction in which a semiconductor layer is formed between the first and second laser array structures, a thickness of the semiconductor layer is adjusted so that the first and second distribution regions contact or overlap with each other.

The above constructions may also include a construction in which an optical waveguide layer which is interposed between the first and second laser array structures, and introduces laser beams oscillated by each of the first and second laser oscillation units, wherein the first and second distribution regions contact or overlap with each other within the optical waveguide layer. The optical waveguide layer is made of a material whose refractive index is larger than that of the clad layer or the like but smaller than that of the active layer. Here, the refractive indexes can be easily controlled by appropriately adjusting a composition of semiconductor materials (the amount of Al or the like).

Here, in the above constructions, at least adjacent two laser oscillation units among the first laser oscillation units are optically coupled with each other, and at least adjacent two laser oscillation units among the second laser oscillation units are optically coupled with each other.

Here, in the above constructions, the first and second current blocking materials fill the spaces so as to form a plurality of first and second stripes, respectively, the optical coupling in the first laser oscillation units is conducted by means of coupling waveguides, each coupling waveguide is formed by removing a part of each of the first stripes in a stripe groove shape, and the optical coupling in the second laser oscillation units is conducted by means of coupling waveguides, each coupling waveguide is formed by removing a part of each of the second stripes in a stripe groove shape.

Here, in the above constructions, the optical coupling of the first laser oscillation units is conducted by allowing adjacent laser oscillation units to merge with each other, and the optical coupling of the second laser oscillation units is conducted by allowing adjacent laser oscillation units to merge with each other.

Here, in the above constructions, the first laser oscillation units has a plurality of first stripe-shaped patterns which are extended from one end facet of the apparatus and a plurality of second stripe-shaped patterns which are extended from the other end, the first and second stripe-shaped patterns are alternately arranged along the vertical direction to their longitudinal direction, and the optical coupling of the first laser oscillation units is conducted between the first and second stripe-shaped patterns, the second laser oscillation units has a plurality of third stripe-shaped patterns which are extended from one end facet of the apparatus and a plurality of fourth stripe-shaped patterns which are extended from the other end, the third and fourth stripe-shaped patterns are alternately arranged along the vertical direction to their longitudinal direction, and the optical coupling of the second laser oscillation units is conducted between the third and fourth stripe-shaped patterns.

Here, in the above constructions, the optical coupling of the first laser oscillation units is conducted by allowing the first distribution regions to contact or overlap with each other, and the optical coupling of the second laser oscillation units is conducted by allowing the first distribution regions to contact or overlap with each other.

Here, the above constructions further include a first electrode which has a first polarity, and which sandwiches the first laser array structure and the second laser array structure; and a second electrode which has a second polarity opposite to the first polarity, and which is formed on both end portions of a top surface of a conductive layer located between the first laser array structure and the second laser array structure.

Here, the above constructions further include a window mirror structure which prevents heat generation and which is formed at end portions of the apparatus where the end portions of the first laser array structure and the second laser array structure face respectively.

This construction prevents the optical absorption at the end facets of the laser oscillation units, which prevents heat generation there.

Here, the above constructions further include an insulating unit which is formed at portions where an electric power is applied to the surface of the window mirror structure.

This construction further prevents heat generation.

Here, in the above constructions, forbidden bands of the first and second current blocking materials are wider than those of active layers in the first and second laser oscillation units respectively, and refractive-indexes of the first and second current blocking materials are smaller than those of the first and second laser oscillation units.

This construction enables a distribution region of laser beams to expand by reducing the optical absorption at the current blocking layer, whereby it becomes easy to optically couple adjacent optical oscillation units with each other.

The first object is also achieved by the manufacturing method for the semiconductor laser array apparatus made up of: a first step for forming the first laser array structure in which the plurality of first laser oscillation units are arranged side by side; and a second step for forming the second laser array structure in which the plurality of second laser oscillation units are arranged side by side so that a top surface of the second laser array structure faces a top surface of the first laser array structure, wherein, in the second step, the second laser array structure is formed on the first laser array structure according to an MOCVD method or an MBE method.

The first object is also achieved by the manufacturing method for the semiconductor laser array apparatus made up of: a first step for forming the first laser array structure in which the plurality of first laser oscillation units are arranged side by side; and, a second step for forming the second laser array structure in which the plurality of second laser oscillation units are arranged side by side so that a top surface of the second laser array structure faces a top surface of the first laser array structure, wherein, in the second step, after the optical waveguide layer is formed on the first laser array structure according to an MOCVD method or an MBE method, the second laser array structure is formed according to the same method.

The first object is also achieved by the manufacturing method for the semiconductor laser array apparatus made up of: a first step for forming the first laser array structure in which the plurality of first laser oscillation units are arranged side by side; a second step for forming the second laser array structure in which the plurality of second laser oscillation units are arranged side by side; and a third step for attaching the first laser array structure to the second array structure. (method A)

The first object is also achieved by the manufacturing method for the semiconductor laser array apparatus made up of: a first step for forming the first laser array structure in which the plurality of first laser oscillation units are arranged side by side; a second step for forming the second laser array structure in which the plurality of second laser oscillation units are arranged side by side; and a third step for attaching the first laser array structure to the second array structure, wherein, the third step follows a step for forming an optical waveguide layer on at least one surface of the first and second laser array structures (method B).

The first object is also achieved by the above manufacturing method A for the semiconductor laser array apparatus further including a fourth step for conducting hydrophilic treatment to at least one surface of surfaces of the first and second laser array structures, prior to the third step, wherein heat treatment is conducted in the presence of hydrogen in the third step.

The first object is also achieved by the above manufacturing method B for the semiconductor laser array apparatus further including a fourth step for conducting hydrophilic treatment to at least one surface among surfaces of the optical waveguide layer, and the first and second laser array structures, prior to the third step, wherein heat treatment is conducted in the presence of hydrogen in the third step.

The second object is achieved by a multi-wavelength laser emitting apparatus made up of: a plurality of semiconductor laser array apparatuses which emit laser beams of different wavelength from each other; and an optical element which condenses the plurality of laser beams into a predetermined position; wherein at least one semiconductor laser array apparatus includes a plurality of laser array structures, each of which includes a plurality of laser oscillation units arranged side by side at an interval and a current blocking material filling the interval between each pair of adjacent laser oscillation units, and at least two adjacent laser array structures, among the plurality of laser array structures, are optically coupled with each other.

Here, it is preferable that the above multi-wavelength laser emitting apparatus further includes an adjusting means which adjusts a position where laser beams are condensed by shifting the optical element; a laser driving means which selects a laser array structure which emits laser beams of a designated wavelength and activates the selected laser array structure; and a control means which controls the adjusting means in accordance with the designated wavelength.

The above-stated semiconductor laser array apparatuses may be applied to this multi-wavelength laser emitting apparatus.

BRIEF DESCRIPTION OF THE DRAWINGS

These and the other objects, advantages and features of the invention will become apparent from the following description thereof taken in conjunction with the accompanying drawings which illustrate a specific embodiment of the invention.

In the drawings:

FIGS. 3 to 5 show the processes by which an element in the semiconductor laser array apparatus is manufactured in this order;

DESCRIPTION OF THE PREFERRED EMBODIMENTS

The following describes a preferred embodiment of the present invention using the drawings.

<Embodiment 1>

Figure 1:
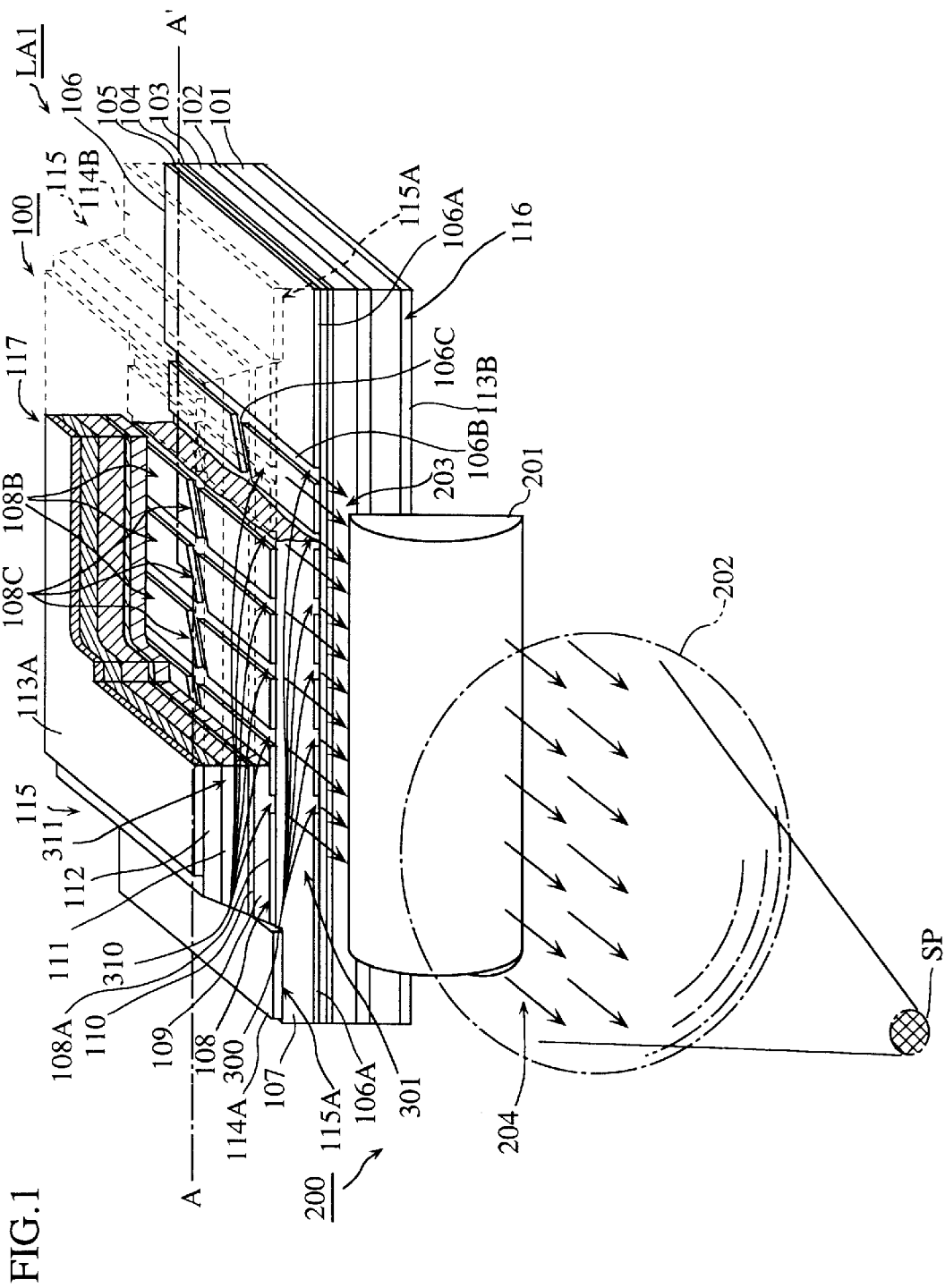
FIG. 1 is a perspective view showing a whole construction of a semiconductor laser array apparatus according to the first embodiment of the present invention.
Figure 2:
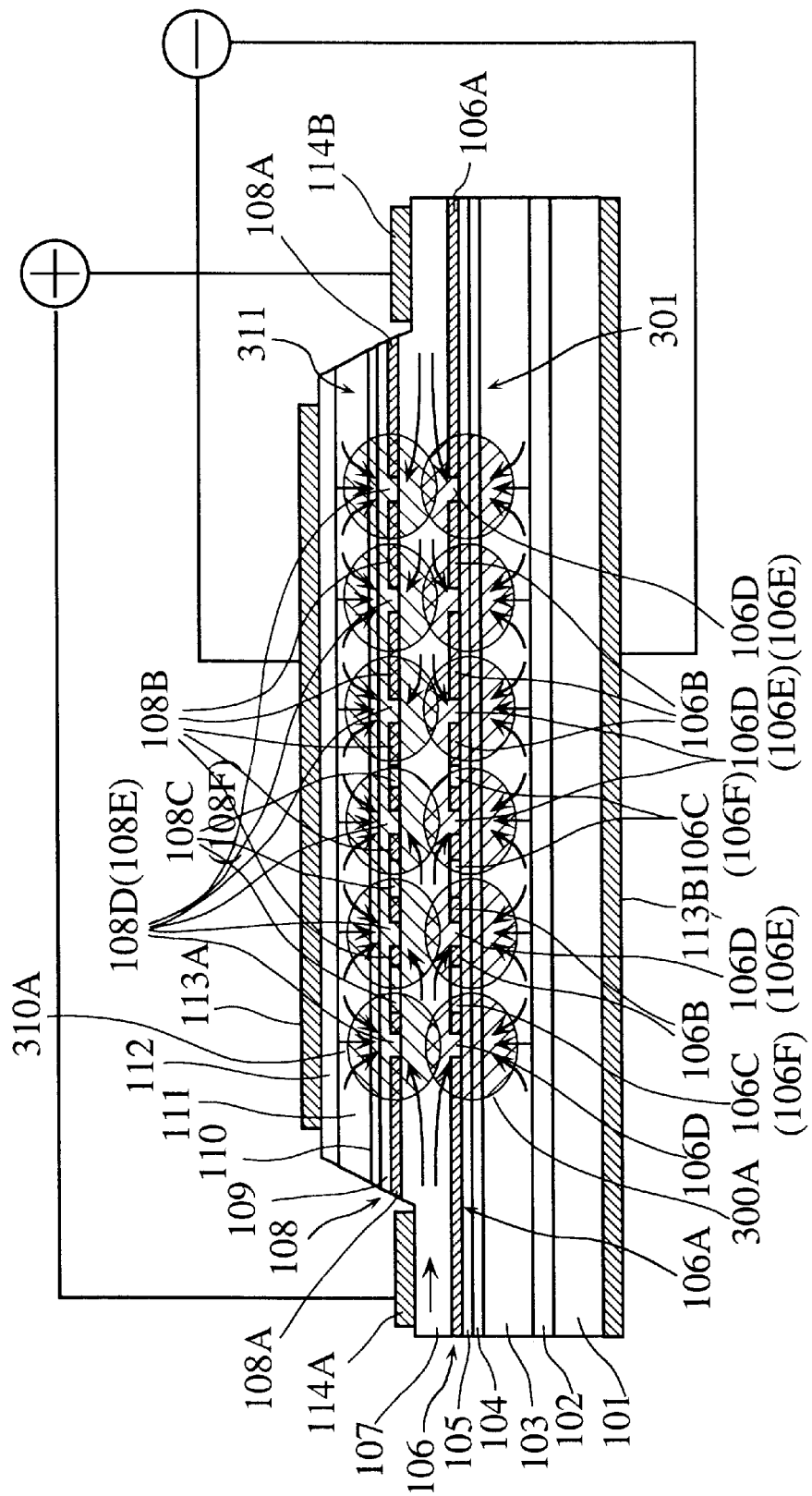
FIG. 2 is a vertical sectional view in FIG. 1.

FIG. 1 is a perspective view showing a construction of a semiconductor laser array apparatus LA1 according to a preferred embodiment of the invention, and FIG. 2 is a vertical sectional view taken on line A–A' in FIG. 1.

<Overall Construction>

The semiconductor laser array apparatus LA1 comprises a semiconductor laser array element 100 having a real refractive index guided self-aligned structure (RISA structure) and oscillating a laser beam of a wavelength corresponding to red, in which a plurality of single heterostrucutre members are fabricated on the same substrate, and an optical unit 200 condensing a plurality of laser beams into one spot.

The semiconductor laser array element 100 is configured so that two stripe-shaped laser oscillation units 300 and 310 are stacked on the same substrate in the vertical direction to the substrate, in which so-called single heterostructure members are laminated. In addition, a plurality of laser oscillation units 300 (310) are arranged side by side on the same layer and in the parallel direction to the substrate. Here, the portion where a plurality of laser oscillation units 300 are arranged side by side in the parallel direction to the substrate is called a first laser array structure 301, while the portion above the first laser array structure 301 and where a plurality of laser oscillation units 301 are arranged side by side in the parallel direction to the substrate is called a second laser array structure 311.

More specifically, the semiconductor laser array element 100 comprises a structure in which an n-type GaAs substrate 101, an n-type GaAs buffer layer 102, an n-type AlGaInP first clad layer 103, a GaInP/AlGaInP quantum well structured first active layer 104, a p-type AlGaInP second clad layer 105, an n-type AlInP first current blocking layer 106, a p-type AlGaInP third clad layer 107, an n-type AlInP second current blocking layer 108, a p-type AlGaInP fourth clad layer 109, a GaInP/AlGaInP quantum well structured second active layer 110, an n-type AlGaInP fifth clad layer 111, an n-type GaAs contact layer 112 are laminated in this order, n-type electrodes 113A and 113B, and p-type electrodes 114A and 114B. Here, the structure other than the electrodes are hereafter called an array structure for the sake of convenience.

The n-type electrodes 113A and 113B are sheet type electrodes provided on the top and bottom surface of the array structure. The n-type electrode 113A is a three-layered electrode made of AuGe/Ni/Au placed at the top surface, while the n-type electrode 113B is a three-layered electrode made of AuGe/Ni/Au placed at the bottom surface (at the substrate side).

A pair of p-type electrodes 114A and 114B are strip shaped electrodes placed at right and left end portions of the array structure and on the surface 115A in two step portions 115 formed by removing both right and left ends of the array structure from the top surface to the vicinity of middle portion of the p-type AlGaInP third clad layer 107.

By means of the above structure, the laser oscillation unit 300 consists of a portion between the n-type AlGaInP first clad layer 103 and the p-type AlGaInP third clad layer 107, while the laser oscillation unit 310 consists of a portion between the p-type AlGaInP third clad layer 107 and the n-type AlGaInP fifth clad layer 111.

The optical unit 200 comprises a collimator lens 201 and a condenser lens 202. The collimator lens functions so that a plurality of laser beams 203 emitted from the both laser oscillation units 300 and 310, which are located at upper and lower portions in the semiconductor laser array element 100, becomes parallel to each other. The condenser lens 202 functions so that a plurality of parallel laser beams 204 from the collimator lens 201 are condensed into a spot SP. Here, as for the collimator lens 202, it is preferable to employ a collimator lens which so that an optical path difference can be corrected in order not to cause a phase shift of the condensed laser beams.

<Detailed Construction>

The following describes the first laser array structure 301 and the second laser array structure 311 in detail.

As shown in FIGS. 1 and 2, the n-type AlInP first current blocking layer 106 consists of both ends portions 106A, a plurality of stripe portions 106B which have a discontiguous portion 106C in the middle thereof along the longitudinal direction and which are provided so as to be parallel to each other. The p-type AlGaInP third clad layer 107 is formed so as to be embedded into the discontiguous portions 106C and stripe-shaped grooves 106D formed between the end element 106A and stripe element 106B and between stripe elements 106B, and to cover all over the current blocking layer 106.

Next, the n-type AlInP second current blocking layer in the second laser array structure 311 placed above the first laser array structure 301 consists of both ends portions 108A and a plurality of stripe portions 108B which have a discontiguous portion 108C in the middle thereof along the longitudinal direction and provided so as to be parallel to each other in the same manner as the above n-type AlInP first current blocking layer 106. The p-type AlGaInP fourth clad layer 109 is formed so as to be embedded into the discontiguous portions 108C and stripe-shaped grooves 108D formed between the end element 108A and stripe element 108B and between stripe elements 108B, and to cover all over the current blocking layer 108.

By means of the construction as stated above, the laser oscillation units 300 and 310 including a region where laser beams are distributed consists of the portions including the active layers, the n-type clad layers and so on in the laser array structures.

In order to oscillate laser beams, an electric power is applied to the portions of the clad layers embedded in the grooves 106D and 108D, and the distinguous portions 106C and 108C through portions above and below them. Then, these grooves 106D and 108D, and the distinguous portions 106C and 108C where the clad layers are embedded becomes a part of waveguides for laser beams. Hereafter, corresponding portions to the groove 106D and the distinguous portion 106C in the first laser array structure 301 are called a main waveguide 106E and a coupling waveguide 106F respectively, while the corresponding portions to the groove 108D and the distinguous portion 108C in the second laser array structure 311 are called a main waveguide 108E and a coupling waveguide 108F respectively.

Next, the following describes a physical relationship between the first laser array structure 301 and the second laser array structure 311.

The physical relationship between these structures 301 and 311 is determined so that the laser oscillation units 300 and 310 are located in the same position in the vertical direction to the substrate and are arranged parallel to each other. In addition, a distribution region 300A of the laser beam emitted from the laser oscillation unit 300 and a distribution region 310A of the laser beam emitted from the laser oscillation unit 310 at least contact or overlap with each other. FIG. 2 shows a state where the distribution regions overlap with each other. Note that, in this and the other embodiments of the invention, distribution regions of laser beams includes the region where a laser beam is leaked into the current blocking layer from the laser oscillation unit. Here, the thickness of the p-type AlGaInP third clad layer 107 is specified.

More specifically, an energy of each laser oscillation unit is normally distributed so that an energy level is the highest in the active layer and gradually decreases with the distance from the active layer. In view of this condition, the regions, whose energy are approximately 10% of that in the center of the distribution regions 300A and 310A of laser beams from the laser oscillation units 300 and 310, overlap with each other by means of the above-stated physical relationship.

As above, the laser oscillation units 300 and 310 are located close to each other the distribution region 300A of the laser beam from the laser oscillation unit 300 contacts or overlap with the distribution region 310A of the laser beam from the laser oscillation unit 310, whereby laser beams emitted from the laser oscillation units can be easily condensed by means of a common optical unit as stated above.

In addition, the materials of the following parts are selected so that the forbidden band widths of the first and second current blocking layers are larger than those of portions of active layers under the portions of the third and fourth clad layers 107 and 109 embedded between elements of the first current blocking layer and between elements of the second current blocking layer, and refractive indexes of the first and second current blocking layers are smaller than the laser oscillation units located between the elements of the first current blocking layer and between patterns of the second current blocking layer.

By means of the above construction, optical confinement effects can be obtained using a difference in real refractive indexes, while enabling an optical loss to reduce due to the absorption of laser beams into the current blocking layers.

Next, laser beams are emitted from an end facet 116 of the semiconductor laser array apparatus in the front side of FIG. 1. A film having a low reflection coefficient of the order of 1–15% is formed on the surface of the end facet 116 so that laser beams do not emit from the opposite end facet 117. Although $Al_2O_3$, $SiO_2$, $Si_3N_4$, $TiO_2$, and so on can be used as a material of the low-reflectance film, it is not limited to such materials. Meanwhile, a film having a high reflection coefficient of the order of 70–98% is formed on the surface of the end facet 117. Although this high-reflectance film is formed by alternatively laminating a low refractive dielectric layer whose material is selected among $Al_2O_3$, $SiO_2$, $Si_3N_4$, and so on, and a high refractive dielectric layer whose material is selected among $TiO_2$, a-Si, hydrogenated a-Si, and so on, in two or more layers, it is not limited to such a construction.

<Manufacturing Method for the Semiconductor Laser Array Element 100>

Figure 5:
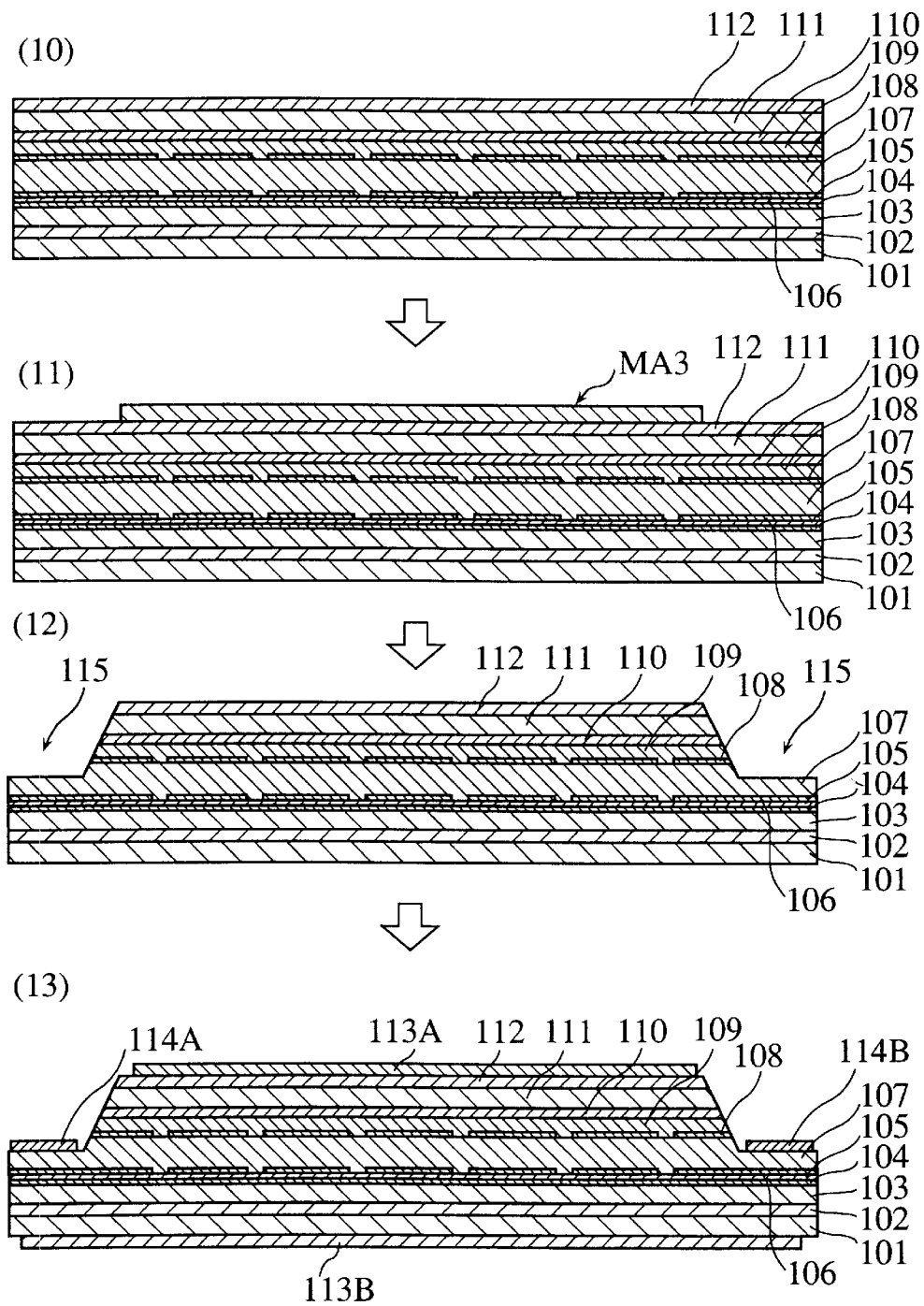

FIGS. 3 to 5 show the processes of manufacturing the semiconductor laser array element 100.

Firstly, as shown in FIG. 3(1), an n-type GaAs substrate 101 is prepared.

Next, as shown in FIG. 3(2), each of layers from an n-type GaAs buffer layer to a p-type AlGaInP second clad layer 105 is sequentially laminated on the n-type GaAs substrate 101 according to an MOCVD method or an MBE method. Each layer in the following processes is formed using the MOCVD method or the MBE method, which will not be described.

Next, as shown in FIG. 3(3), a material layer 106G to which patterning is performed to form an n-type InAlP first current blocking layer 106 is formed.

Next, as shown in FIG. 3(4), a mask layer MA1 is formed, whose pattern is an opposite pattern to the intended pattern of the n-type InAlP first current blocking layer 106.

Next, as shown in FIG. 3(5), a liquid-phase etching is performed to unmasked portions, so that the pattern of the n-type InAlP first current blocking layer 106 is formed. Thereafter, the mask layer MA1 is removed.

Next, as shown in FIG. 4(6), a p-type AlGaInP third clad layer is formed.

Next, as shown in FIG. 4(7), a material layer 108G for an n-type InAlP second current blocking layer 108 is formed.

Next, as shown in FIG. 4(8), a mask layer MA2 is formed, whose pattern is an opposite pattern to the intended pattern of the p-type InAlP second current blocking layer 108.

Next, as shown in FIG. 4(9), a liquid-phase etching is performed to unmasked portions, so that the pattern of the n-type InAlP second current blocking layer 108 is formed into the material layer 108G. Thereafter, the mask layer MA2 is removed.

Next, as shown in FIG. 5(10), each layer from a p-type AlGaInP fourth clad layer 109 to an n-type GaAs contact layer 112 is sequentially laminated.

Next, as shown in FIG. 5(11), a mask layer MA3 is formed on the top surface of the n-type GaAs contact layer 112 other than both right and left end portions.

Next, as shown in FIG. 5(12), a liquid-phase etching is performed to unmasked portions, so that both right and left end portions of each layer from the n-type GaAs contact layer 112 to the middle portion of the p-type AlGaInP third clad layer located below to form the step portion 115. Thereafter, the mask layer MA3 is removed.

According to the above-stated processes, the array structure is formed.

Finally, as shown in FIG. 5(13), n-type electrodes 113A and 113B, and p-type electrodes 114A and 114B are formed at the predetermined positions respectively to complete the semiconductor laser array apparatus.

<Function and Effects of the Semiconductor Laser Array Apparatus LA1>

According to the semiconductor laser array apparatus LA1 in the above construction, laser beams do not interfere with each other so as to cancel each other out due to the phase shift at the spot where laser beams are condensed. Therefore, a high-power laser spot can be obtained in accordance with the number of installed laser oscillation units.

This is because phase locking is performed within each laser array structure and between different laser array structures.

Firstly, the reason why phase locking are possible within each of the first laser array structure 301 and the second laser array structure 311 will be described.

Figure 6:
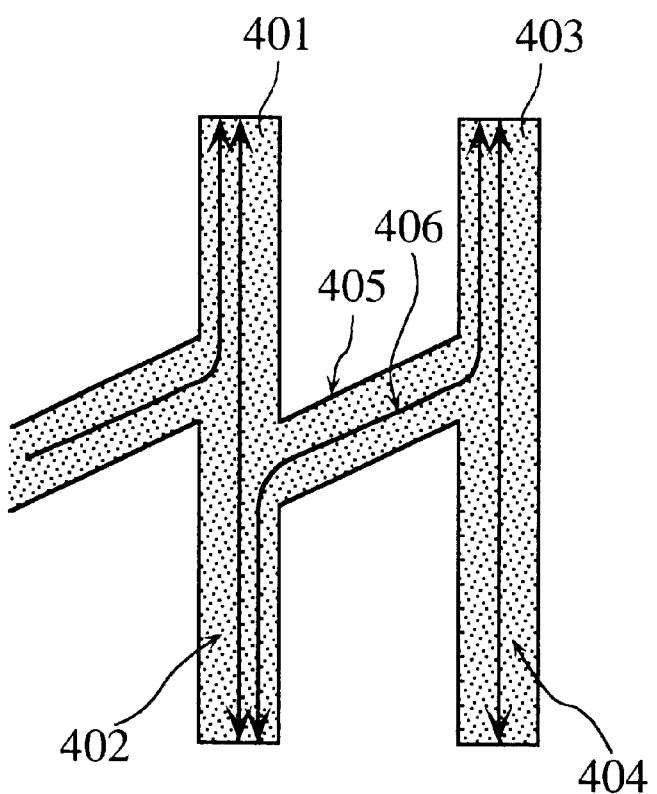
FIG. 6 is a schematic diagram showing a function of sharing resonators in the semiconductor laser array apparatus in detail.

FIG. 6 is a schematic diagram to explain the above-stated effect (i.e., a resonator shared effect) in detail.

As previously stated, adjacent main waveguides 106E and 108E are coupled with each other by means of the coupling waveguides 106F and 108F. Therefore, it can be regarded as the state where so-called a resonator is shared.

That is, a resonator 402 formed with a main waveguide 401 in the longitudinal direction thereof and a resonator 404 formed with the other main waveguide 403 adjacent to the waveguide 401 in the longitudinal direction thereof are coupled with each other by means of a coupling waveguide 405. Therefore, it can be considered as a whole that a resonator 406 is formed so as to share a part of the resonators 402 and 404 and include a coupling waveguide 405, in addition to the resonators 402 and 404.

As a result, laser beams guided through adjacent main waveguides 401 and 402 interfere with each other, while the resonator is formed across the main waveguides 401 and 402. By a synergistic effect in accordance with those effects, both wavelengths and phases of laser beams in the main waveguides can be matched with each other, so that phase locking can be performed with stability and reliability.

As stated above, phase locking can be performed between adjacent main waveguides in each of the first and second laser array structures 301 and 311. Naturally, phase locking is performed in a plurality of main waveguides in each of the first and second laser array structures 301 and 311 in the same manner.

Meanwhile, laser oscillation units 300 and 310 in the first laser array structure 301 and the second laser array structure 311 are located so that the distribution regions 300A and 310A of their laser beams contact or overlap with each other. Therefore, it can be considered that phase locking can be performed, because laser beams from upper and lower laser oscillation units 300 and 310 interfere with each other.

Consequently, phase locking can be performed for laser beams emitted from all laser oscillation units.

<Physical Relationship Between the First Laser Array Structure 301 and the Second Laser Array Structure 311>

If only the distribution regions of laser beams from the first and second laser array structures 301 and 311 at least contact or overlap with each other, then the laser beams interfere with each other.

Therefore, laser oscillation units in each laser array structure are not necessarily located in the same position in the vertical direction to the substrate and parallel to each other.

For example, laser oscillation units 300 and 310 may be located to be displaced from each other in the vertical direction to the substrate.

In addition, it may be configured so that distribution regions of laser beams from a laser oscillation unit 300 located at the right end of the first laser array structure 301 and a laser oscillation unit 301 located at the left end of the second laser array structure 311 only contact or overlaps with each other at one part. This is because phase locking can be performed between adjacent laser oscillation units in the same laser array structure (301 or 311) by means of the coupling waveguide as stated above.

Moreover, it may be configured so that the laser oscillation units 300 and 301 in the first and second laser array structures 301 and 311 are located so as not to be parallel to each other but to cross each other.

<Embodiment 2>

A semiconductor laser array apparatus in embodiment 2 is different from that of embodiment 1 in that it is formed by bonding two structures prepared in advance and including a first laser array structure 301 and a second laser array structure 311 respectively, whereas the semiconductor laser array apparatus in embodiment 1 is configured so that each layer is integrally formed according to the MOCVD or MBE method. The following describes difference points between them.

Figure 7:
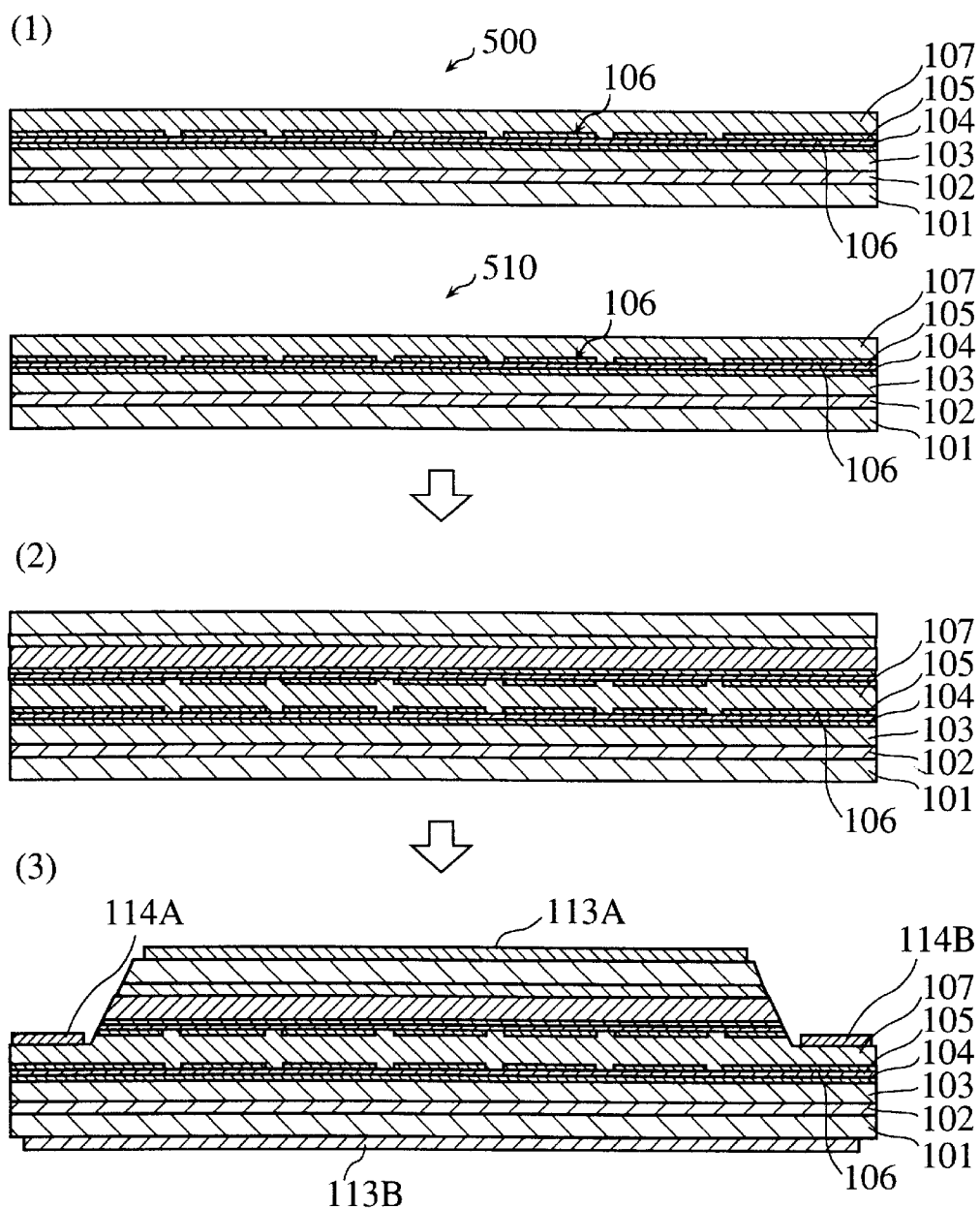
FIG. 7 shows one of processes by which an element in a semiconductor laser array apparatus according to the second embodiment of the present invention is manufactured in this order.

FIG. 7 shows processes by which the apparatus according to embodiment 2 is manufactured.

Firstly, as shown in FIG. 7(1), array structures 500 and 510 are manufactured according to the processes between FIGS. 3(1)–4(6).

Next, as shown in FIG. 7(2), the array structures 500 and 510 are superimposed so that their two p-type AlGaInP third clad layers are opposed to each other and laser oscillation units of them are aligned in the vertical direction to the substrate. Then heat treatment is conducted to adhere them according to hydrogen bond.

Prior to this process, the surfaces of the p-type AlGaInP third clad layers 107 in the two array structures 500 and 510 which are subjected to bonding should be cleaned to remove a natural oxidation film. Then, hydrophilic treatment is conducted by which hydroxyl groups are surfaced. It is desirable to superimpose array structures after the hydrophilic treatment, because they are integrated by hydrogen bond even in the room temperature, which leads to improve mechanical strength between bonded faces.

Moreover, if heat treatment is conducted in the presence of hydrogen in the above process, the array structures 500 and 510 can be integrated with each other more firmly.

Finally, as shown in FIG. 7(3), the semiconductor laser array apparatus is completed according to the processes between FIGS. 5(10)–5(13).

<Embodiment 3>

A semiconductor laser array apparatus of embodiment 3 has the same construction as in the above semiconductor laser array apparatus LA1, except that shapes of the n-type AlInP first current blocking layer and the n-type AlInP second current blocking layer are different from those in LA1. The following describes difference points between them.

Figure 8:
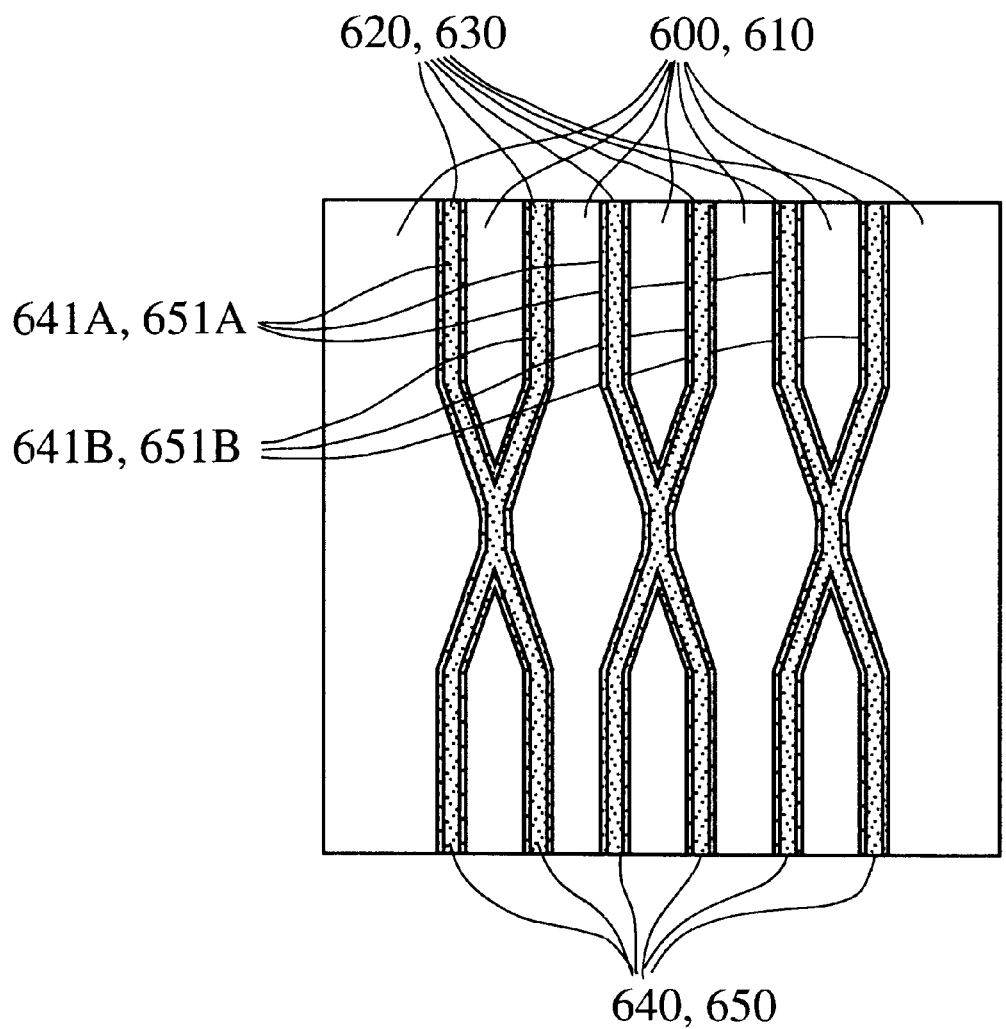
FIG. 8 is a plan view showing a main construction element in a semiconductor laser array apparatus according to the third embodiment of the present invention.

FIG. 8 is a top plan view showing shapes of an n-type AlInP first current blocking layer 600 and an n-type AlInP second current blocking layer 610 in the semiconductor laser array apparatus according to embodiment 3.

As shown in FIG. 8, waveguides, when looked down on from the top, are configured so as to bend like an X-shape at regions where the n-type AlInP first current blocking layer 600 and the n-type AlInP second current blocking layer 610 are not present, so that the adjacent waveguides merges with each other.

More specifically, the n-type AlInP first and second current blocking layers 600 and 610 comprise a plurality of regions respectively, and a p-type AlGaInP third and fourth clad layers 620 and 630 are embedded between adjacent regions.

The waveguides 640 and 650 which are formed by these embedded portions with clad layers are shaped so as to merge with each other in the middle of their longitudinal directions like a letter X. As stated above, the waveguides 640 and 650, which are formed between the adjacent regions of the n-type AlInP first current blocking layer 600 and between the adjacent regions of the n-type AlInP second current blocking layer 610 respectively, are called X junction waveguides 640 and 650.

By means of these X junction waveguides 640 and 650, laser beams interfere with each other at the merging point of adjacent waveguides 641A and 651A (shown in the left side in FIG. 8), and waveguides 641B and 651B (shown in the right side in the same), and resonators can be partially shared.

In addition, in case that a plurality of X junction waveguides 640 and 650 are provided to be parallel with each other, adjacent and not merged waveguides are positioned close to each other so that distribution regions of laser beams from them contact or overlap with each other in the horizontal direction. Therefore, laser beams interfere with each other even between the adjacent and not merged waveguides. As a result, resonance can be produced among all waveguides.

Thus, phase locking can be performed for each main waveguide, whereby laser beams do not interfere with each other so as to cancel each other out. Consequently, a high power laser spot according to the number of laser oscillation units can be obtained.

<Embodiment 4>

A semiconductor laser array apparatus of embodiment 4 has the same construction as in the above semiconductor laser array apparatus LA1, except that shapes of the n-type AlInP first current blocking layer and the n-type AlInP second current blocking layer are different from those in LA1. The following describes difference points between them.

Figure 9:
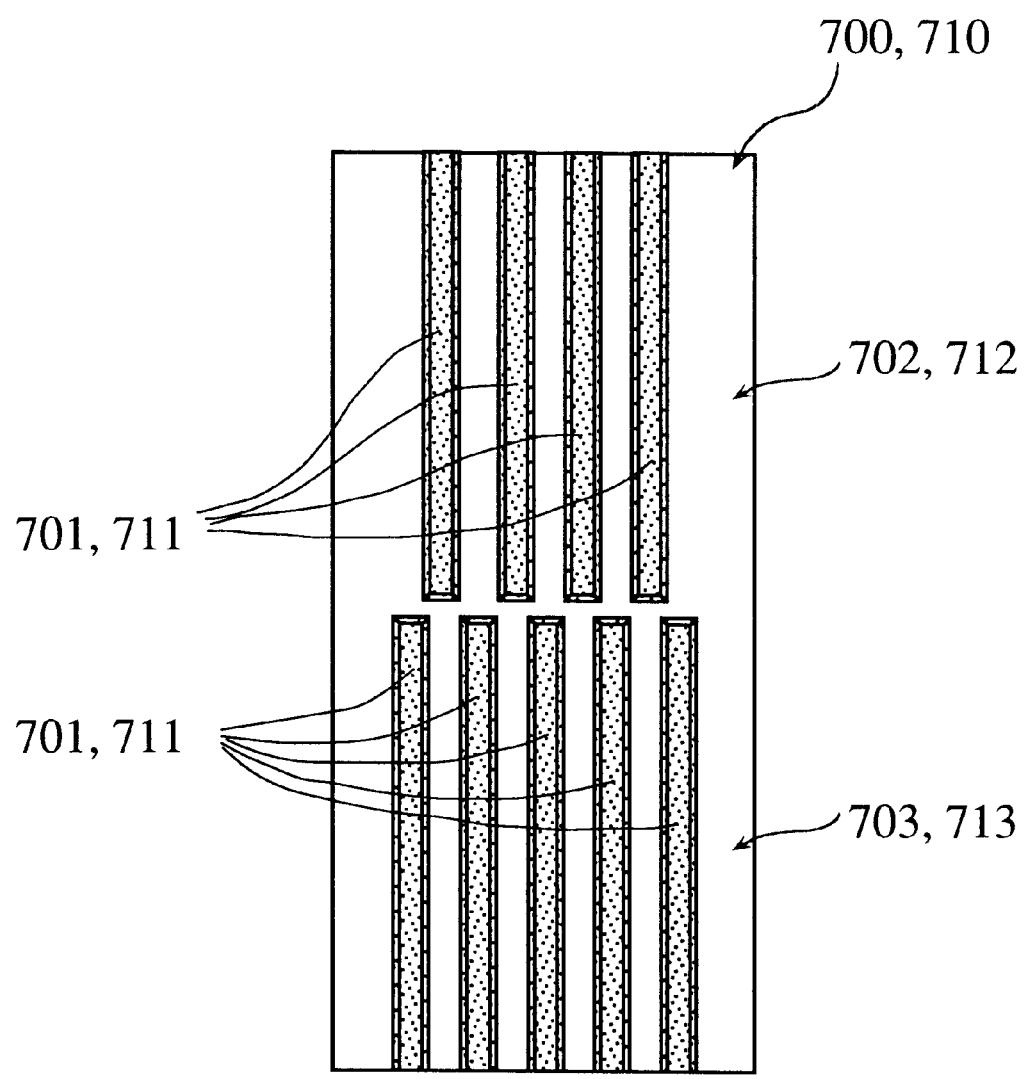
FIG. 9 is a plan view showing a main construction element in a semiconductor laser array apparatus according to the fourth embodiment of the present invention.

FIG. 9 is a top plan view showing shapes of an n-type AlInP first current blocking layer 700 and an n-type AlInP second current blocking layer 710 in the semiconductor laser array apparatus according to the embodiment 4.

The n-type AlInP first and second current blocking layers 700 and 710 do not comprise a plurality of regions as in the above embodiment, but they are in contiguous sheet forms, where a plurality of short and long grooves 701 and 711 are formed so as to be parallel to each other in specific patterns. Then, p-type AlGaInP third and fourth clad layers are embedded in the grooves 701 and 711, respectively.

More specifically, the pattern in which the p-type AlGaInP third and fourth clad layers are embedded (i.e., the pattern of grooves 701 and 711) consists of stripes 702/703 and 712/713, which extend parallel to each other from either end portion to the vicinity of middle portion. In addition, each of these stripes 702/703 and 712/713 is positioned so as to have different phases. Besides, the distances between the stripes 702 and 703, and the stripes 712 and 713 are set so that their waveguide regions (regions where laser beam are leaked into the current blocking layers) contact or overlap with each other.

While, the stripes 712, where the p-type AlGaInP fourth clad layer extended from one end of the apparatus is embedded into the current blocking layer, and the stripe 713 where the p-type AlGaInP fourth clad layer extended from the other end of the apparatus is embedded into the current blocking layer waveguide regions are located so that their distribution regions contact or overlap with each other between the stripes 712 and the stripes 713.

The above construction allows laser beams to interfere with each other between waveguides 702 and 703, and 712 and 713, which are extended from different end facets. Therefore, phase locking can be performed for laser beams oscillated from each laser oscillation unit, so that laser beams do not interfere with each other so as to cancel each other out due to the phase shift at the spot where the laser beams are condensed. Consequently, a high-power laser spot can be obtained in accordance with the number of installed laser oscillation units.

<Embodiment 5>

A semiconductor laser array apparatus of embodiment 5 has the same construction as in the above semiconductor laser array apparatus LA1, except that shapes of the n-type AlInP first current blocking layer and the n-type AlInP second current blocking layer, and the distance between adjacent laser oscillation units 300 and between those units 310 respectively are different from those in LA1. The following describes difference points between them.

Figure 10:
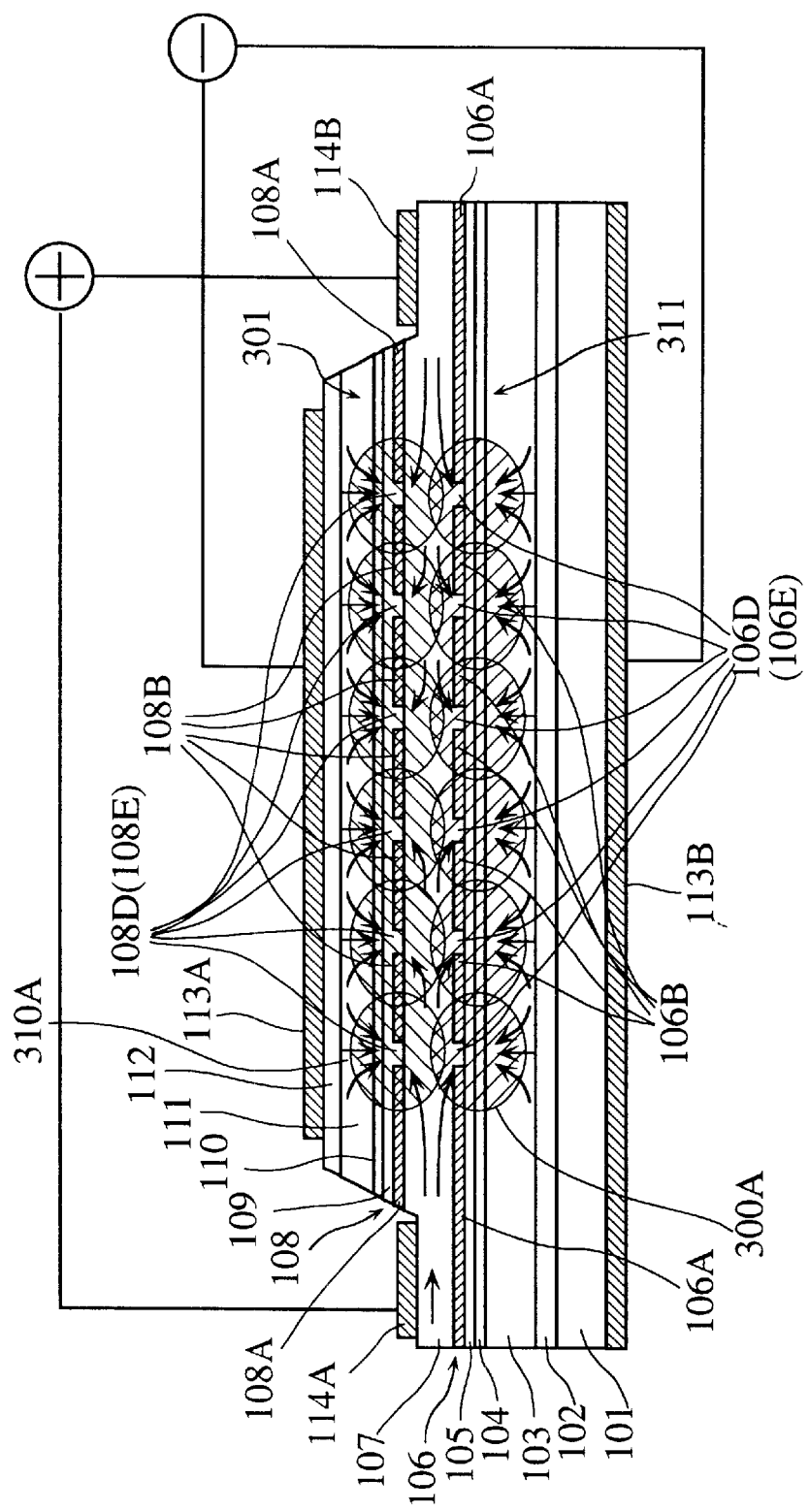
FIG. 10 is a sectional view of an element according to the fifth embodiment of the present invention, which corresponds to FIG. 2.

FIG. 10 is a sectional view of an semiconductor laser array apparatus according to the fifth embodiment, which corresponds to FIG. 2.

Although the distinguous portions are formed in the middle of the current blocking layers in the first and second laser array structure 301 and 311 respectively in the first embodiment, those portion are not formed but they have usual shapes in which extended stripe shapes are contiguously formed.

In addition, stripes are narrower than those of the first embodiment, except in both ends regions of current blocking layers, whereby laterally adjacent laser oscillation units 300 and 310 respectively become closer to each other.

The laterally adjacent laser oscillation units are positioned by specifying the width of the current blocking elements so that laterally adjacent distribution regions 300A (310A) of laser beams from laterally adjacent laser oscillation units 300 (310) contact or overlap with each other.

More specifically, the regions whose energy are approximately 10% of that in the center region of the distribution regions 300A and 310A of laser beams from the laser oscillation units 300 and 310 overlap with each other by means of the above-stated physical relationship in the same manner as in the above embodiment.

Thus, phase locking can be performed for laser beams in the same laser array structure by allowing distribution regions of laser beams from horizontally adjacent laser oscillation units to contact or overlap with each other.

Here, the interval between laterally adjacent laser oscillation units in each laser array structure may be either fixed or varied, which will be described in the following.

Firstly, the amount of emitted light tends to be smaller in the center portion than in the both ends portions, because it is hard to supply an electric power to the center portion.

In view of addressing such a problem, it is desirable to narrow the interval between laser oscillation units as they near to the center portion in order to increase the amount of light therein.

Next, the heating value is larger in the center portion than in the both ends portions, because it is hard to dissipate heat in the center portion.

In view of addressing such a problem, it is desirable to widen the interval between laser oscillation units as they near to the center portion, which prevents heat from being trapped in the narrow region and reduces the heating value in the center portion.

<Embodiment 6>

A semiconductor laser array apparatus of embodiment 6 has the same construction as in the above semiconductor laser array apparatus LA1, except that an optical waveguide layer is interposed between the first laser array structure and the second laser array structure in order to condense their laser beams into their center portions. The following describes difference points between them.

Figure 11:
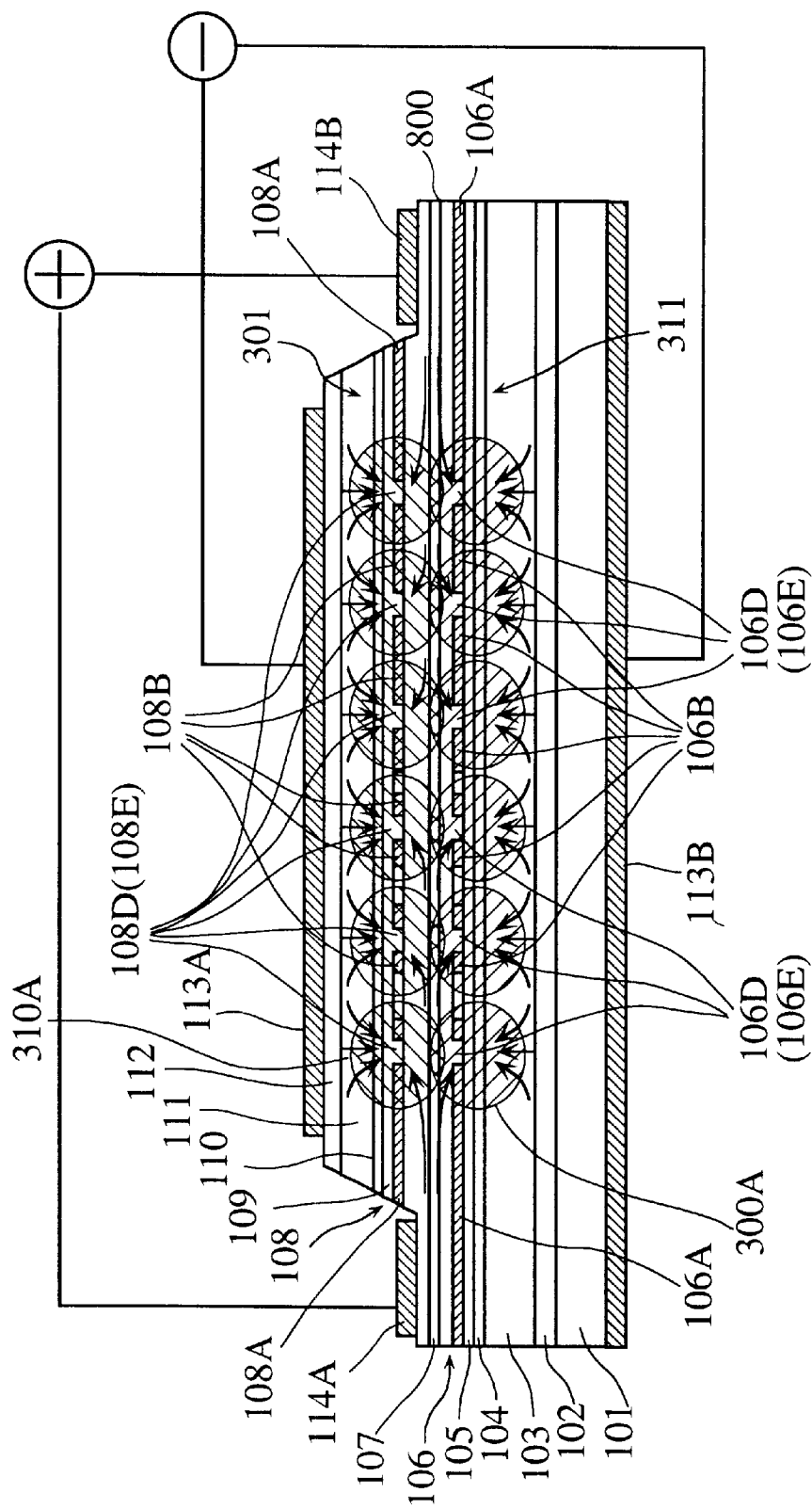
FIG. 11 is a sectional view of an element according to the sixth embodiment of the present invention, which corresponds to FIG. 2.

FIG. 11 is a sectional view of an semiconductor laser array element according to the sixth embodiment, which corresponds to FIG. 2.

As shown in FIG. 11, a p-type AlGaInP optical waveguide layer 800 is inserted in the vertically center portion of the p-type AlGaInP third clad layer 107.

Thereby, the p-type AlGaInP optical waveguide layer is interposed between the first laser array structure and the second laser array structure.

The composition and amount of impurities of the p-type AlGaInP optical waveguide layer 800 is specified so that its bandgap and refractive index are not smaller than those of the active layer and not larger than those of the p-type AlGaInP third clad layer 107.

This p-type AlGaInP optical waveguide layer 800 enables laser beams oscillated from upper and lower laser oscillation units to condense into this layer (800). Therefore, as shown in FIG. 11, distribution regions of laser beams from upper and lower laser oscillation units can overlap in the optical waveguide layer, which is the same as in the first embodiment.

As a result, phase locking can be performed by allowing laser beams from the corresponding upper and lower laser oscillation units to interfere with each other.

In addition, there is an another advantage that distribution regions of laser beams from the upper and lower structures can be unified, so that they are easy to be condensed into one point.

Although their manufacturing methods will not be described in detail, it can be fabricated by adding a process of manufacturing the p-type AlGaInP optical waveguide layer 800, in the process of forming the p-type AlGaInP third clad layer 107 as shown in FIG. 4(6).

The difference between the optical coupling method in the first and sixth embodiments are as follows.

The semiconductor laser array apparatus of the first embodiment is adopted the optical coupling method (hereafter called "method A") by which the distance between the first and second laser array structures (i.e., the thickness of the clad layer between those layers) are specified so that distribution regions of laser beams from laser oscillation units contact or overlap with each other.

On the contrary, this embodiment adopts the optical method (hereafter called "method B") which does not depend on the distance between the first and second laser array structures, but in which laser beams are condensed into the optical waveguide layer provided between the laser oscillation units.

Thus, in the method B, it is necessary that the optical waveguide layer is positioned so that the distribution regions of laser beams from upper and lower laser oscillation units contact or overlap with each other in this layer. However, there is an advantage of reducing design constraints to narrow the distance between the first and second laser array structures.

In addition, when both methods A and B are combined so that the upper and lower laser oscillation units become close to each other, while forming an optical waveguide layer of an optimum thickness interposed between those layers, laser beams from those laser oscillation units can be condensed into approximately one spot.

By means of the above construction, it becomes easy to condense laser beams from the semiconductor laser array apparatus into one spot.

Here, it is possible to condense laser beams from the laser oscillation units which are arranged upper and lower portions in the apparatus into almost one spot either by the method A or B. However, it can be achieved easily by combining those methods.

<Embodiment 7>

A semiconductor laser array apparatus of the embodiment 7 is different from the above-stated semiconductor laser array apparatus LA1 in that window mirror structures are formed at facets where both ends in the longitudinal direction of the laser oscillation unit in the semiconductor laser array apparatus face, and an insulating layer is formed at the top surface of each electrode positioned at regions where the window mirror structures are formed. The following describes difference points between them.

Figure 12:
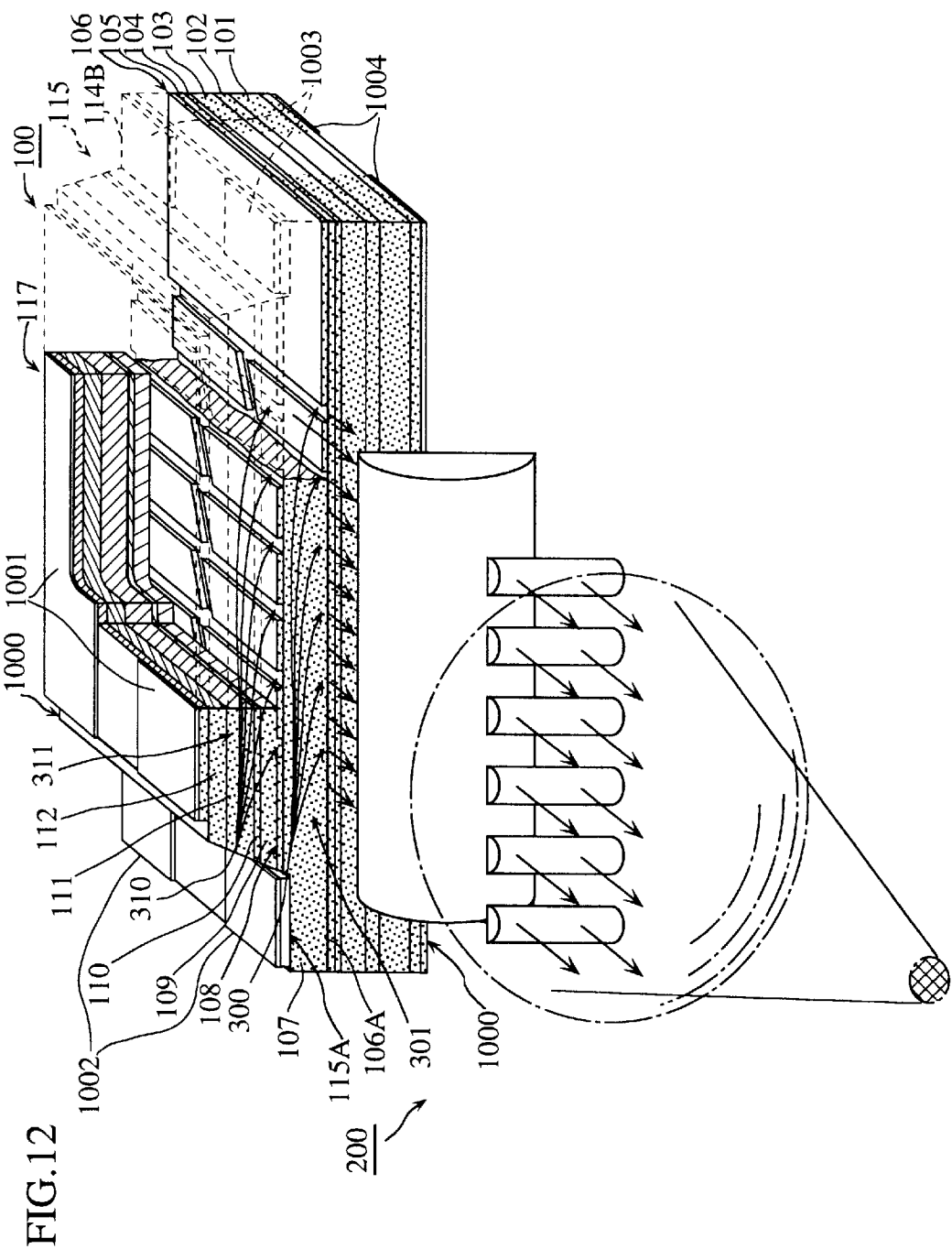
FIG. 12 is a perspective view showing a construction of a semiconductor laser array apparatus according to the seventh embodiment of the present invention.

FIG. 12 is a perspective view showing a construction of a semiconductor laser array apparatus according to the seventh embodiment.

As shown in FIG. 12, Zn is diffused at the regions where the both ends in the longitudinal direction of the laser oscillation units 300 and 310 face, so that a Zn diffusion portion 1000 is formed. This Zn diffusion portion 1000 forms the window mirror structure. This structure prevents laser beams from being absorbed at both ends of the laser oscillation units 300 and 310 in order not to generate heat there.

In addition, SiO$_2$ insulating layers 1001, 1002, 1003, and 1004 are formed on the electrodes beneath which this Zn diffusion portion 1000 are formed. This structure further prevents an electric power from being applied at the end facets in order not to generate heat.

Here, the above-stated semiconductor laser array apparatus is configured so that the p-type AlGaInP second clad layer and the n-type AlInP first current blocking layer, and the p-type AlGaInP third clad layer and the n-type AlInP second current blocking layer directly contact with each other. However, a p-type InGaP etching stop layer can be formed between them. This p-type InGaP etching stop layer prevents oxidation of the surface of the current blocking layers. Therefore, current blocking layers with excellent crystalline structures can be formed.

Meanwhile, although a pair of collimator lens and condenser lens are used as the optical unit 200, a hologram may be substituted for them. This makes a construction of the optical unit compact.

Alternatively, although a red semiconductor laser is exemplified in this embodiment, it is naturally possible that this construction is applied to blue, green, infrared semiconductor lasers and the like.

Finally, although the two laser oscillation units are stacked in this embodiment, three or more units can be stacked. Thereby, much higher light output power can be realized.

<Embodiment 8>

The following explains modifications of the above-stated semiconductor laser array apparatus.

Figure 13:
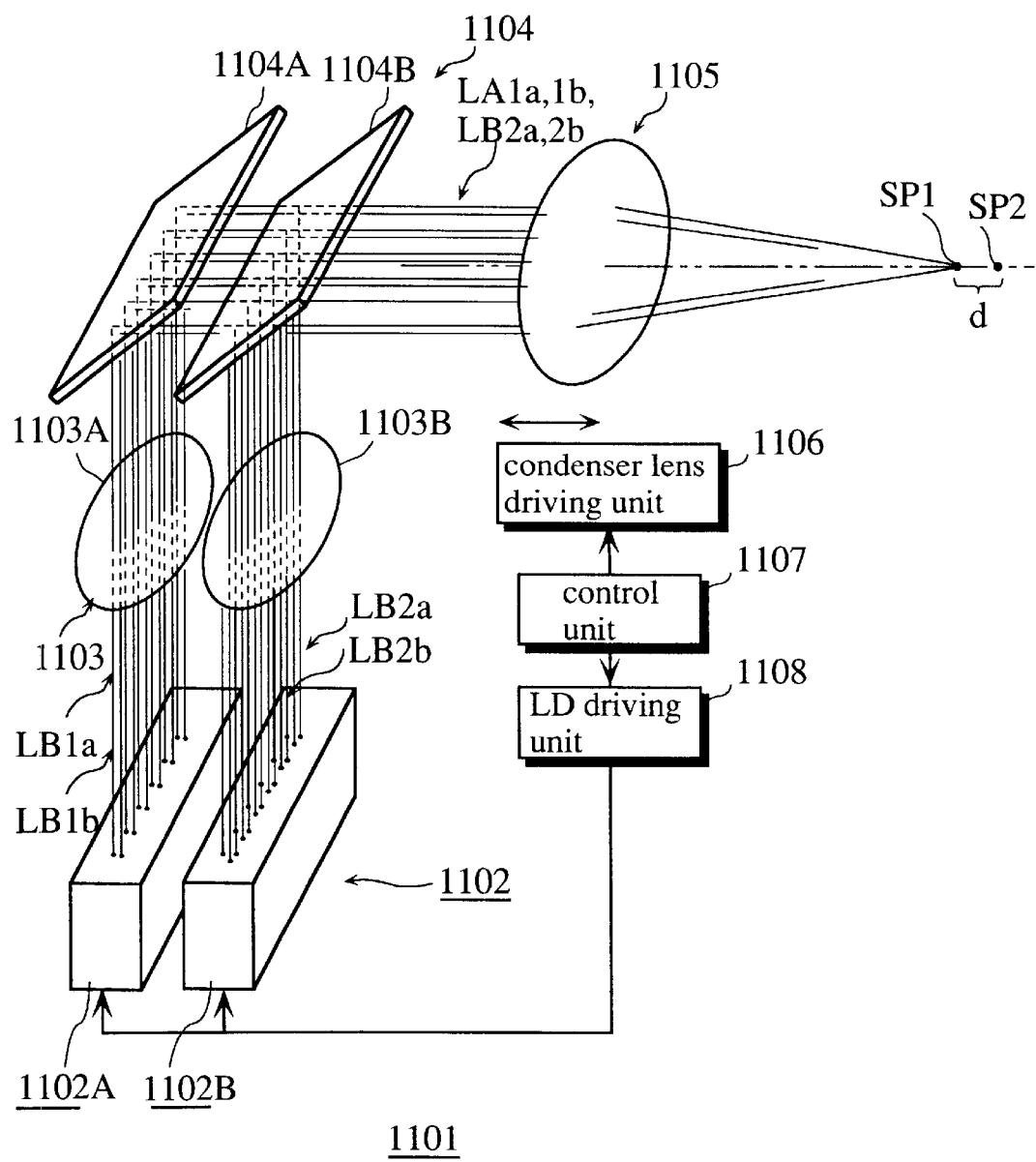
FIG. 13 is a perspective view showing an overall construction of a multi-wavelength laser emitting apparatus according to the eighth embodiment of the present invention.

FIG. 13 is a perspective view showing a construction of main elements of a multi-wavelength laser emitting apparatus according to the eighth embodiment.

As shown in FIG. 13, the multi-wavelength laser emitting apparatus 1101 comprises a light source unit 1102 emitting laser beams LB1 and LB2 whose wavelength are different from each other and consisting of semiconductor laser array apparatuses 1102A and 1102B, a collimate unit 1103 making laser beams LB1*a* and LB1*b* and LB2*a* and LB2*b*, which are emitted from the apparatuses 1102A and 1102B, parallel to each other, a reflecting unit 1104 reflecting laser beams LB1*a*, LB1*b*, LB2*a*, and LB2*b* so that all of them move parallel to each other in the same direction, a condenser lens 1105 condensing parallel laser beams LB1*a*, LB1*b*, LB2*a*, and LB2*b* into a predetermined condensing position on the optical axis, a condenser lens driving unit 1106 shifting the condenser lens 1105 along the optical axis, a control unit 1107 controlling the operation of the condenser lens driving unit 1106, and so on. Here, the condenser lens normally consists of a plurality of lenses. However, one condenser lens 1105 is shown in this embodiment.

The light source unit 1102 is configured so that the semiconductor laser array apparatuses 1102A and 1102B are arranged in parallel, which emits a plurality of laser beams LB1*a* and LB1*b*, and LB2*a* and LB2*b* moving in parallel with each other and whose wavelength are different from each other (i.e., wavelength is different between LB1 and LB2).

The composition of the active layers in the semiconductor laser array apparatus 1102A and 1102B are different from each other, so that they emit laser beams with wavelengths corresponding to red and infrared regions, respectively. Each of a plurality of laser beams LB1*a*, LB1*b* (red), and LB2*a* and LB2*b* (infrared) from the same apparatus (1102A and 1102B) are emitted in a state where their phases and wavelengths are matched with each other (phase locking state). Thereby, a high-power laser beam can be obtained.

The laser beams LB1*a* and LB1*b*, and LB2*a* and LB2*b* enter into hologram optical components 1103A and 1103B in the collimate unit 1103, respectively. The hologram optical components 1103A and 1103B are designed so as to make incident light, which diffuse after emitted from point light sources, parallel to each other. Thereby, laser beams passing through the hologram optical components 1103A and 1103B becomes parallel to each other. Here, a collimate lens may be used as a means for making laser beams parallel to each other.

The reflecting unit 1104 comprises a mirror 1104A reflecting parallel laser beams LB1 to the direction of the condenser lens 1105, and a half mirror 1104B reflecting parallel laser beams LB2 to the same direction. The half mirror 1104B is a well-known optical component for allowing a part of incident light to pass through, while reflecting the other part of light according to the incidence angle. In this case, this half mirror is fixed to a position so that main laser beams of LB1*a*, LB1*b*, LB2*a*, and LB2B form an angle of 45 degrees with respect to its incidence plane.

Thereby, laser beams LB1 reflected by the mirror 1104A pass through the half mirror 1104B, so that they moves parallel to the laser beams LB2 reflected by the half mirror 1104B to the direction of the condenser lens 1105. This enables laser beams LB1 and LB2 emitted from the different positions to move to the same direction, while most of laser beams are overlapped.

As stated above, the condenser lens 1105 functions so as to condense the incident laser beams LB1*a*, LB1*b*, LB2*a*, and LB2*b* into a predetermined condensing point on the optical axis. Here, as is generally known, this condensing point on the optical axis varies in accordance with the difference in the wavelengths of incident light (longitudinal chromatic aberration). Therefore, their image formation points are different; a point SP1 (red) and a point SP2 (infrared).

Then, the apparatus of this embodiment is configured so that the position of the condenser lens 1105 can be adjusted along the optical direction according to the wavelength of a used laser. Thereby, when a laser beam of a different wavelength is used, a beam waist position of the laser beam does not fluctuate and an stable processing can be obtained. That is, the condenser lens 1105 is supported to be movable along the optical axis and the condenser lens driving unit 1106 shifts this lens 1105 along the axis in accordance with the wavelength of a used laser, so that the condensing point of laser beams can be fixed regardless of their wavelength.

For instance, when the laser beam is changed from red to infrared, the condenser lens 1105 is shifted by d (shown in FIG. 13) towards the reflecting unit 1104 along the optical axis in order to always condense laser beams into the spot SP1.

Here, the condenser lens driving unit 1106 includes a well-known fine adjustable linear actuator, such as a screw feed mechanism using ball screws. In case that the condenser lens consists of a plurality of lenses, the condensing position of laser beams can be adjusted by shifting at least one of those lenses along the optical axis.

The control unit 1107 functions so as to control a travel of the lens driven by the condenser lens driving unit 1106, while controlling laser beams from the semiconductor laser array apparatuses 1102A and 1102B through a laser diode (LD) driving unit 1108. This unit switches on and off the semiconductor laser array apparatuses 1102A and 1102B so that a laser beam with a specified wavelength is outputted in accordance with the application. Moreover, the control unit 1107 includes a program containing a travel data of the condenser lens varying from each semiconductor laser array apparatus, in advance. Therefore, the condensing position of laser beams can be fixed regardless of the wavelengths of laser beams. In case that a stepping motor is used to drive the condenser lens driving unit 1106, a travel can be easily controlled by the number of the driving pulses.

Figure 14:
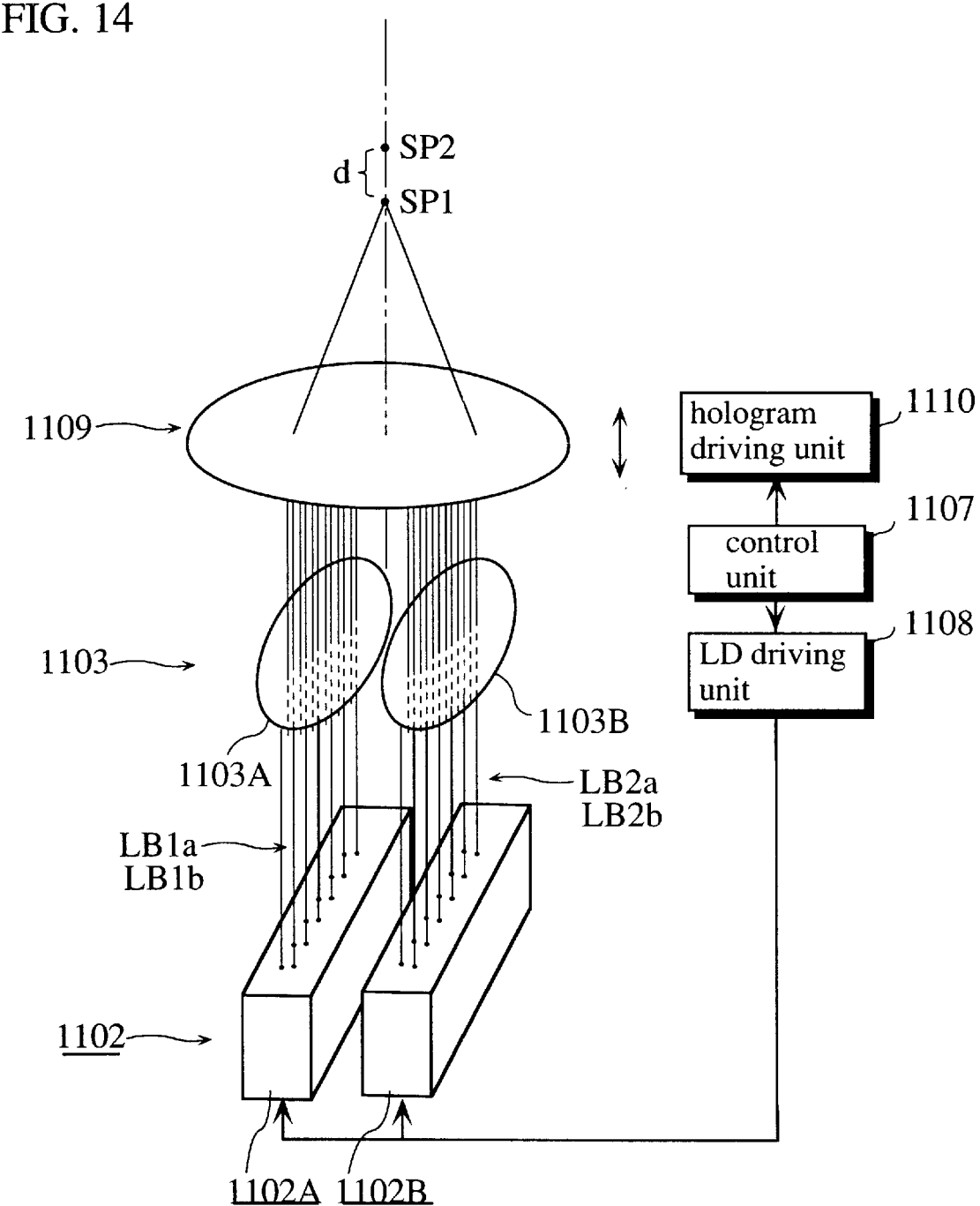
FIG. 14 is a perspective view showing an overall construction of a multi-wavelength laser emitting apparatus according to a modification of the eighth embodiment of the present invention.

FIG. 14 shows a modification of the multi-wavelength laser emitting apparatus according to the eighth embodiment. This apparatus is different from that in FIG. 13, in that the reflecting unit 1104 is removed and a hologram optical component 1109, which has a light condensing function, is provided in place of the condenser lens 1105. Since the hologram optical component 1109 has an advantage to be immune to optical distortion even when its diameter becomes large, there is no need to make laser beams LB1 and LB2 move in almost the same optical path by means of the half mirror 1104B as in FIG. 13. Instead, laser beams may enter to the hologram optical component 1109 with their interval maintained, which leads to downsizing for the apparatus. Besides, this leads to reduction of the number of components and manufacturing processes, resulting in reduction of the cost. Moreover, an optical loss in laser beams LB1*a*, LB1*b*, LB2*a*, and LB2*b* is large in the construction in FIG. 13, where the half mirror is used, because the half mirror 1104B reflects a part of laser beams and allows the other part of laser beams to pass through. However, this modification does not have such a problem, so that electric powers can be saved.

However, longitudinal chromatic aberration occurs in this construction also. Therefore, it is necessary that the hologram optical component 1109 is shifted along the optical axis according to the wavelength of emitted laser beams by a hologram driving unit 1110 in order to fix the condensing point of laser beams. Since the construction for adjusting is in the same manner as FIG. 13, the description will be omitted.

EXAMPLE APPLICATIONS

Finally, examples of applications using the above semiconductor laser array apparatus will be described. Naturally, they are not limited to the following examples.

(1) Red laser made of AlGaInP (wavelength: 655 through 665 nm)

(a) The above semiconductor laser array apparatus may be incorporated into a welding torch in order to weld metals. Laser beams from the welding apparatus has a high power, as well as being colored, so that it has such an excellent viewability to improve the workabitliy of welding. In addition, it may be applied to apparatuses for punching and cutting printed boards or the like. Besides, it may be applied to apparatuses for surface treatment, such as quenching or the like.

Moreover, it may be applied to an apparatus for welding with weaving used for sheet-metal welding of a car body, in which welding is performed while periodically and laterally oscillating a front end unit of a robot. In this case, incorporated the above high-power semiconductor laser array apparatus into a torch, the welding with weaving can be rapidly performed.

(b) It is effective to use the semiconductor laser array apparatus of the present invention to produce two-dimensional data matrix data, such as two-dimensional data matrix codes that can be processed with a spot light. Although conventionally this is performed by a YAG laser, there is a problem in rapidly forming a uniform dot pattern, because the response of YAG laser is slow. For instance, it is not suitable for forming a matrix pattern, to which a pulse of light is frequently applied after a time interval. On the contrary, since the response of the red semiconductor laser is fast, it is effective for forming such a matrix pattern.

(c) The above semiconductor laser may be applied to medical equipment used for surgical operations, a laser scalpel for hemostasis, treatment against malignant tumor such as cancer, in which laser beams are irradiated to the living body after injection of photofrin, hair restoration treatment, and so on.

(2) Blue laser made of InGaN (wavelength 550 nm; $In_{0.5}Ga_{0.5}N$)

This laser may be applied for treatment for detached retinas by irradiating the light to the cornea.

(3) Green laser made of InGaN (wavelength 380 nm; $In_{0.5}Ga_{0.95}N$)

This laser may be applied for treatment for myopia by irradiating the light to the cornea.

(4) Infrared laser made of InGaAs (wavelength 1060 nm; $In_{0.2}Ga_{0.9}As$)

In addition to the welding, punching, surface treatment, marking, surgical operations, and laser scalpels for hemostasis, this laser may be applied for treatment for detached retinas by irradiating the light to the cornea via an SHG element, which reduces a wavelength to the half, or the like.

Meanwhile, Although the present invention has been fully described by way of examples with reference to the accompanying drawings, it is to be noted that various changes and modifications will be apparent to those skilled in the art. Therefore, unless such changes and modifications depart from the scope of the present invention, they should be construed as being included therein.

What is claimed is:

1. A semiconductor laser array apparatus, comprising:
  a first laser array structure which includes,
    a plurality of first laser oscillation units which are arranged side by side at an interval, and
    a first current blocking material which fills a space between each pair of adjacent first laser oscillation units; and,
  a second laser array structure which includes,
    a plurality of second laser oscillation units which are arranged side by side at an interval, and
    a second current blocking material which fills a space between each pair of adjacent second laser oscillation units,
  wherein, when the semiconductor laser array apparatus is activated, laser beams generated by the first laser array structure and the second laser array structure leak to the outside of the first and second laser array structures so as to form first and second distribution regions of the laser beams,
  and the first and second laser array structures are closely disposed so that the first and second distribution regions contact or overlap with each other.

2. The semiconductor laser array apparatus of claim 1, wherein a semiconductor layer is formed between the first and second laser array structures,
  a thickness of the semiconductor layer is adjusted so that the first and second distribution regions contact or overlap with each other.

3. The semiconductor laser array apparatus of claim 2, wherein at least adjacent two laser oscillation units among the first laser oscillation units are optically coupled with each other,
  and at least adjacent two laser oscillation units among the second laser oscillation units are optically coupled with each other.

4. The semiconductor laser array apparatus of claim 2, further comprising:
  a first electrode which has a first polarity opposite to the first polarity, and which sandwiches the first laser array structure and the second laser array structure; and
  a second electrode which has a second polarity opposite to the first polarity, and which is formed on both end portions of a top surface of a conductive layer located between the first laser array structure and the second laser array structure.

5. The semiconductor laser array apparatus of claim 2, wherein,
  forbidden bands of the first and second current blocking materials are wider than those of active layers in the first and second laser oscillation units respectively, and
  refractive-indexes of the first and second current blocking materials are smaller than those of the first and second laser oscillation units.

6. The semiconductor laser array apparatus of claim 1, further comprising:
  an optical waveguide layer which is interposed between the first and second laser array structures, and introduces laser beams oscillated by each of the first and second laser oscillation units,
  wherein the first and second distribution regions contact or overlap with each other within the optical waveguide layer.

7. The semiconductor laser array apparatus of claim 6, wherein at least adjacent two laser oscillation units among the first laser oscillation units are optically coupled with each other,
  and at least adjacent two laser oscillation units among the second laser oscillation units are optically coupled with each other.

8. The semiconductor laser array apparatus of claim 7, wherein the first and second current blocking materials fill the spaces so as to form a plurality of first and second stripes, respectively,
  the optical coupling in the first laser oscillation units is conducted by means of coupling waveguides, each coupling waveguide is formed by removing a part of each of the first stripes in a stripe groove shape,
  and the optical coupling in the second laser oscillation units is conducted by means of coupling waveguides, each coupling waveguide is formed by removing a part of each of the second stripes in a stripe groove shape.

9. The semiconductor laser array apparatus of claim 8, further comprising:
  a first electrode which has a first polarity, and which sandwiches the first laser array structure and the second laser array structure; and
  a second electrode which has a second polarity opposite to the first polarity, and which is formed on both end portions of a top surface of a conductive layer located between the first laser array structure and the second laser array structure.

10. The semiconductor laser array apparatus of claim 9, further comprising:
  a window mirror structure which prevents heat generation and which is formed at end portions of the apparatus where the end portions of the first laser array structure and the second laser array structure face respectively.

11. The semiconductor laser array apparatus of claim 10, further comprising:
  an insulating unit which is formed at portions where an electric power is applied to the surface of the window mirror structure.

12. The semiconductor laser array apparatus of claim 7, wherein the optical coupling of the first laser oscillation units is conducted by allowing adjacent laser oscillation units to merge with each other,
  and the optical coupling of the second laser oscillation units is conducted by allowing adjacent laser oscillation units to merge with each other.

13. The semiconductor laser array apparatus of claim 12, further comprising:
  a first electrode which has a first polarity, and which sandwiches the first laser array structure and the second laser array structure; and
  a second electrode which has a second polarity opposite to the first polarity, and which is formed on both end portions of a top surface of a conductive layer located between the first laser array structure and the second laser array structure.

14. The semiconductor laser array apparatus of claim 13, further comprising:
  a window mirror structure which prevents heat generation and which is formed at end portions of the apparatus where the end portions of the first laser array structure and the second laser array structure face respectively.

15. The semiconductor laser array apparatus of claim 14, further comprising:
an insulating unit which is formed at portions where an electric power is applied to the surface of the window mirror structure.

16. The semiconductor laser array apparatus of claim 7, wherein the first laser oscillation units has a plurality of first stripe-shaped patterns which are extended from one end facet of the apparatus and a plurality of second stripe-shaped patterns which are extended from the other end, the first and second stripe-shaped patterns are alternately arranged along the vertical direction to their longitudinal direction, and
the optical coupling of the first laser oscillation units is conducted between the first and second stripe-shaped patterns,
the second laser oscillation units has a plurality of third stripe-shaped patterns which are extended from one end facet of the apparatus and a plurality of fourth stripe-shaped patterns which are extended from the other end, the third and fourth stripe-shaped patterns are alternately arranged along the vertical direction to their longitudinal direction, and
the optical coupling of the second laser oscillation units is conducted between the third and fourth stripe-shaped patterns.

17. The semiconductor laser array apparatus of claim 16, further comprising:
a first electrode which has a first polarity, and which sandwiches the first laser array structure and the second laser array structure; and
a second electrode which has a second polarity opposite to the first polarity, and which is formed on both end portions of a top surface of a conductive layer located between the first laser array structure and the second laser array structure.

18. The semiconductor laser array apparatus of claim 17, further comprising:
a window mirror structure which prevents heat generation and which is formed at end portions of the apparatus where the end portions of the first laser array structure and the second laser array structure face respectively.

19. The semiconductor laser array apparatus of claim 18, further comprising:
an insulating unit which is formed at portions where an electric power is applied to the surface of the window mirror structure.

20. The semiconductor laser array apparatus of claim 7, wherein the optical coupling of the first laser oscillation units is conducted by allowing the first distribution regions to contact or overlap with each other, and
the optical coupling of the second laser oscillation units is conducted by allowing the first distribution regions to contact or overlap with each other.

21. The semiconductor laser array apparatus of claim 20, further comprising:
a first electrode which has a first polarity, and which sandwiches the first laser array structure and the second laser array structure; and
a second electrode which has a second polarity opposite to the first polarity, and which is formed on both end portions of a top surface of a conductive layer located between the first laser array structure and the second laser array structure.

22. The semiconductor laser array apparatus of claim 21, further comprising:
a window mirror structure which prevents heat generation and which is formed at end portions of the apparatus where the end portions of the first laser array structure and the second laser array structure face respectively.

23. The semiconductor laser array apparatus of claim 22, further comprising:
an insulating unit which is formed at portions where an electric power is applied to the surface of the window mirror structure.

24. The semiconductor laser array apparatus of claim 7, wherein,
forbidden bands of the first and second current blocking materials are wider than those of active layers in the first and second laser oscillation units respectively, and
refractive-indexes of the first and second current blocking materials are smaller than those of the first and second laser oscillation units.

25. The semiconductor laser array apparatus of claim 6, further comprising:
a first electrode which has a first polarity, and which sandwiches the first laser array structure and the second laser array structure; and
a second electrode which has a second polarity opposite to the first polarity, and which is formed on both end portions of a top surface of a conductive layer located between the first laser array structure and the second laser array structure.

26. The semiconductor laser array apparatus of claim 25, further comprising:
a window mirror structure which prevents heat generation and which is formed at end portions of the apparatus where the end portions of the first laser array structure and the second laser array structure face respectively.

27. The semiconductor laser array apparatus of claim 26, further comprising:
an insulating unit which is formed at portions where an electric power is applied to the surface of the window mirror structure.

28. The semiconductor laser array apparatus of claim 7, further comprising:
a first electrode which has a first polarity, and which sandwiches the first laser array structure and the second laser array structure; and
a second electrode which has a second polarity opposite to the first polarity, and which is formed on both end portions of a top surface of a conductive layer located between the first laser array structure and the second laser array structure.

29. The semiconductor laser array apparatus of claim 28, further comprising:
a window mirror structure which prevents heat generation and which is formed at end portions of the apparatus where the end portions of the first laser array structure and the second laser array structure face respectively.

30. The semiconductor laser array apparatus of claim 29, further comprising:
an insulating unit which is formed at portions where an electric power is applied to the surface of the window mirror structure.

31. The semiconductor laser array apparatus of claim 6, wherein,
forbidden bands of the first and second current blocking materials are wider than those of active layers in the first and second laser oscillation units respectively, and
refractive-indexes of the first and second current blocking materials are smaller than those of the first and second laser oscillation units.

32. The manufacturing method for the semiconductor laser array apparatus of claim 6, comprising:
- a first step for forming the first laser array structure in which the plurality of first laser oscillation units are arranged side by side; and
- a second step for forming the second laser array structure in which the plurality of second laser oscillation units are arranged side by side so that a top surface of the second laser array structure faces a top surface of the first laser array structure,
- wherein, in the second step, after the optical waveguide layer is formed on the first laser array structure according to an MOCVD method or an MBE method, the second laser array structure is formed according to the same method.

33. The manufacturing method for the semiconductor laser array apparatus of claim 6, comprising:
- a first step for forming the first laser array structure in which the plurality of first laser oscillation units are arranged side by side;
- a second step for forming the second laser array structure in which the plurality of second laser oscillation units are arranged side by side; and
- a third step for attaching the first laser array structure to the second array structure,
- wherein the third step follows a step for forming an optical waveguide layer on at least one surface of the first and second laser array structures.

34. The manufacturing method of claim 33, further comprising:
- a fourth step for conducting hydrophilic treatment to at least one surface among surfaces of the optical waveguide layer, and the first and second laser array structures, prior to the third step,
- wherein heat treatment is conducted in the presence of hydrogen in the third step.

35. The semiconductor laser array apparatus of claim 1,
- wherein at least adjacent two laser oscillation units among the first laser oscillation units are optically coupled with each other,
- and at least adjacent two laser oscillation units among the second laser oscillation units are optically coupled with each other.

36. The semiconductor laser array apparatus of claim 35,
- wherein the first and second current blocking materials fill the spaces so as to form a plurality of first and second stripes, respectively,
- the optical coupling in the first laser oscillation units is conducted by means of coupling waveguides, each coupling waveguide is formed by removing a part of each of the first stripes in a stripe groove shape,
- and the optical coupling in the second laser oscillation units is conducted by means of coupling waveguides, each coupling waveguide is formed by removing a part of each of the second stripes in a stripe groove shape.

37. The semiconductor laser array apparatus of claim 36, further comprising:
- a first electrode which has a first polarity, and which sandwiches the first laser array structure and the second laser array structure; and
- a second electrode which has a second polarity opposite to the first polarity, and which is formed on both end portions of a top surface of a conductive layer located between the first laser array structure and the second laser array structure.

38. The semiconductor laser array apparatus of claim 37, further comprising:
- a window mirror structure which prevents heat generation and which is formed at end portions of the apparatus where the end portions of the first laser array structure and the second laser array structure face respectively.

39. The semiconductor laser array apparatus of claim 38, further comprising:
- an insulating unit which is formed at portions where an electric power is applied to the surface of the window mirror structure.

40. The semiconductor laser array apparatus of claim 35,
- wherein the optical coupling of the first laser oscillation units is conducted by allowing adjacent laser oscillation units to merge with each other,
- and the optical coupling of the second laser oscillation units is conducted by allowing adjacent laser oscillation units to merge with each other.

41. The semiconductor laser array apparatus of claim 40, further comprising:
- a first electrode which has a first polarity, and which sandwiches the first laser array structure and the second laser array structure; and
- a second electrode which has a second polarity opposite to the first polarity, and which is formed on both end portions of a top surface of a conductive layer located between the first laser array structure and the second laser array structure.

42. The semiconductor laser array apparatus of claim 41, further comprising:
- a window mirror structure which prevents heat generation and which is formed at end portions of the apparatus where the end portions of the first laser array structure and the second laser array structure face respectively.

43. The semiconductor laser array apparatus of claim 42, further comprising:
- an insulating unit which is formed at portions where an electric power is applied to the surface of the window mirror structure.

44. The semiconductor laser array apparatus of claim 35,
- wherein the first laser oscillation units has a plurality of first stripe-shaped patterns which are extended from one end facet of the apparatus and a plurality of second stripe-shaped patterns which are extended from the other end, the first and second stripe-shaped patterns are alternately arranged along the vertical direction to their longitudinal direction, and
- the optical coupling of the first laser oscillation units is conducted between the first and second stripe-shaped patterns,
- the second laser oscillation units has a plurality of third stripe-shaped patterns which are extended from one end facet of the apparatus and a plurality of fourth stripe-shaped patterns which are extended from the other end, the third and fourth stripe-shaped patterns are alternately arranged along the vertical direction to their longitudinal direction, and
- the optical coupling of the second laser oscillation units is conducted between the third and fourth stripe-shaped patterns.

45. The semiconductor laser array apparatus of claim 44, further comprising:
- a first electrode which has a first polarity, and which sandwiches the first laser array structure and the second laser array structure; and a second electrode which has a second polarity opposite to the first polarity, and which is formed on both end portions of a top surface of a conductive layer located between the first laser array structure and the second laser array structure.

46. The semiconductor laser array apparatus of claim 45, further comprising:
a window mirror structure which prevents heat generation and which is formed at end portions of the apparatus where the end portions of the first laser array structure and the second laser array structure face respectively.

47. The semiconductor laser array apparatus of claim 46, further comprising:
an insulating unit which is formed at portions where an electric power is applied to the surface of the window mirror structure.

48. The semiconductor laser array apparatus of claim 35, wherein the optical coupling of the first laser oscillation units is conducted by allowing the first distribution regions to contact or overlap with each other, and
the optical coupling of the second laser oscillation units is conducted by allowing the first distribution regions to contact or overlap with each other.

49. The semiconductor laser array apparatus of claim 48, further comprising:
a first electrode which has a first polarity, and which sandwiches the first laser array structure and the second laser array structure; and
a second electrode which has a second polarity opposite to the first polarity, and which is formed on both end portions of a top surface of a conductive layer located between the first laser array structure and the second laser array structure.

50. The semiconductor laser array apparatus of claim 49, further comprising:
a window mirror structure which prevents heat generation and which is formed at end portions of the apparatus where the end portions of the first laser array structure and the second laser array structure face respectively.

51. The semiconductor laser array apparatus of claim 50, further comprising:
an insulating unit which is formed at portions where an electric power is applied to the surface of the window mirror structure.

52. The semiconductor laser array apparatus of claim 35, further comprising:
a first electrode which has a first polarity, and which sandwiches the first laser array structure and the second laser array structure; and
a second electrode which has a second polarity opposite to the first polarity, and which is formed on both end portions of a top surface of a conductive layer located between the first laser array structure and the second laser array structure.

53. The semiconductor laser array apparatus of claim 52, further comprising:
a window mirror structure which prevents heat generation and which is formed at end portions of the apparatus where the end portions of the first laser array structure and the second laser array structure face respectively.

54. The semiconductor laser array apparatus of claim 53, further comprising:
an insulating unit which is formed at portions where an electric power is applied to the surface of the window mirror structure.

55. The semiconductor laser array apparatus of claim 35, wherein,
forbidden bands of the first and second current blocking materials are wider than those of active layers in the first and second laser oscillation units respectively, and
refractive-indexes of the first and second current blocking materials are smaller than those of the first and second laser oscillation units.

56. The semiconductor laser array apparatus of claim 1, further comprising:
a first electrode which has a first polarity opposite to the first polarity, and which sandwiches the first laser array structure and the second laser array structure; and
a second electrode which has a second polarity opposite to the first polarity, and which is formed on both end portions of a top surface of a conductive layer located between the first laser array structure and the second laser array structure.

57. The semiconductor laser array apparatus of claim 56, further comprising:
a window mirror structure which prevents heat generation and which is formed at end portions of the apparatus where the end portions of the first laser array structure and the second laser array structure face respectively.

58. The semiconductor laser array apparatus of claim 57, further comprising:
an insulating unit which is formed at portions where an electric power is applied to the surface of the window mirror structure.

59. The semiconductor laser array apparatus of claim 1, wherein,
forbidden bands of the first and second current blocking materials are wider than those of active layers in the first and second laser oscillation units respectively, and
refractive-indexes of the first and second current blocking materials are smaller than those of the first and second laser oscillation units.

60. The manufacturing method for the semiconductor laser array apparatus of claim 2, comprising:
a first step for forming the first laser array structure in which the plurality of first laser oscillation units are arranged side by side; and
a second step for forming the second laser array structure in which the plurality of second laser oscillation units are arranged side by side so that a top surface of the second laser array structure faces a top surface of the first laser array structure,
wherein, in the second step, the second laser array structure is formed on the first laser array structure according to an MOCVD method or an MBE method.

61. The manufacturing method for the semiconductor laser array apparatus of claim 2, comprising:
a first step for forming the first laser array structure in which the plurality of first laser oscillation units are arranged side by side;
a second step for forming the second laser array structure in which the plurality of second laser oscillation units are arranged side by side; and
a third step for attaching the first laser array structure to the second array structure.

62. The manufacturing method of claim 61, further comprising:
a fourth step for conducting hydrophilic treatment to at least one surface of surfaces of the first and second laser array structures, prior to the third step,
wherein heat treatment is conducted in the presence of hydrogen in the third step.

63. A multi-wavelength laser emitting apparatus, comprising:
a plurality of semiconductor laser array apparatuses which emit laser beams of different wavelength from each other; and
an optical element which condenses the plurality of laser beams into a predetermined position;
wherein at least one semiconductor laser array apparatus includes a plurality of laser array structures, each of which includes a plurality of laser oscillation units arranged side by side at an interval and a current blocking material filling the interval between each pair of adjacent laser oscillation units,
and at least two adjacent laser array structures, among the plurality of laser array structures, are optically coupled with each other.

64. The multi-wavelength laser emitting apparatus of claim 63, further comprising:
an adjusting means which adjusts a position where laser beams are condensed by shifting the optical element;
a laser driving means which selects a laser array structure which emits laser beams of a designated wavelength and activates the selected laser array structure; and
a control means which controls the adjusting means in accordance with the designated wavelength.

65. The multi-wavelength laser emitting apparatus of claim 63,
wherein each of the plurality of semiconductor laser array apparatuses is a semiconductor laser array apparatus, comprising:
a first laser array structure which includes,
a plurality of first laser oscillation units which are arranged side by side at an interval, and
a first current blocking material which fills a space between each pair of adjacent first laser oscillation units; and,
a second laser array structure which includes,
a plurality of second laser oscillation units which are arranged side by side at an interval, and
a second current blocking material which fills a space between each pair of adjacent second lasers oscillation units,
wherein, when the semiconductor laser array apparatus is activated, laser beams generated by the first laser array structure and the second laser array structure leak to the outside of the first and second laser array structures so as to form first and second distribution regions of the laser beams,
and the first and second laser array structures are closely disposed so that the first and second distribution regions contact or overlap with each other.

66. A laser welding apparatus, which uses laser beams emitted from a semiconductor laser array apparatus, comprising:
a first laser array structure which includes,
a plurality of first laser oscillation units which are arranged side by side at an interval, and
a first current blocking material which fills a space between each pair of adjacent first laser oscillation units; and,
a second laser array structure which includes,
a plurality of second laser oscillation units which are arranged side by side at an interval, and
a second current blocking material which fills a space between each pair of adjacent second laser oscillation units,
wherein, when the semiconductor laser array apparatus is activated, laser beams generated by the first laser array structure and the second laser array structure leak to the outside of the first and second laser array structures so as to form first and second distribution regions of the laser beams,
and the first and second laser array structures are closely disposed so that the first and second distribution regions contact or overlap with each other.

67. A two-dimensional matrix data manufacturing apparatus, wherein two-dimensional matrix data is formed by irradiating a target with laser beams emitted from a semiconductor laser array apparatus, comprising:
a first laser array structure which includes,
a plurality of first laser oscillation units which are arranged side by side at an interval, and
a first current blocking material which fills a space between each pair of adjacent first laser oscillation units; and,
a second laser array structure which includes,
a plurality of second laser oscillation units which are arranged side by side at an interval, and
a second current blocking material which fills a space between each pair of adjacent second laser oscillation units,
wherein, when the semiconductor laser array apparatus is activated, laser beams generated by the first laser array structure and the second laser array structure leak to the outside of the first and second laser array structures so as to form first and second distribution regions of the laser beams,
and the first and second laser array structures are closely disposed so that the first and second distribution regions contact or overlap with each other.

68. A semiconductor laser scalpel apparatus, which is used for hemostasis and incising a living body by irradiating the living body with laser beams emitted a semiconductor laser array apparatus, comprising:
a first laser array structure which includes,
a plurality of first laser oscillation units which are arranged side by side at an interval, and
a first current blocking material which fills a space between each pair of adjacent first laser oscillation units; and,
a second laser array structure which includes,
a plurality of second laser oscillation units which are arranged side by side at an interval, and
a second current blocking material which fills a space between each pair of adjacent second laser oscillation units,
wherein, when the semiconductor laser array apparatus is activated, laser beams generated by the first laser array structure and the second laser array structure leak to the outside of the first and second laser array structures so as to form first and second distribution regions of the laser beams,
and the first and second laser array structures are closely disposed so that the first and second distribution regions contact or overlap with each other.

69. A treatment apparatus for tumor, wherein treatment is conducted against tumor by irradiating a living body after injection of photofrin with laser beams emitted from a semiconductor laser array apparatus, comprising:
a first laser array structure which includes,
a plurality of first laser oscillation units which are arranged side by side at an interval, and
a first current blocking material which fills a space between each pair of adjacent first laser oscillation units; and,
a second laser array structure which includes,
a plurality of second laser oscillation units which are arranged side by side at an interval, and a second current blocking material which fills a space between each pair of adjacent second laser oscillation units, wherein, when the semiconductor laser array apparatus is activated, laser beams generated by the first laser array structure and the second laser array structure leak to the outside of the first and second laser array structures so as to form first and second distribution regions of the laser beams, and the first and second laser array structures are closely disposed so that the first and second distribution regions contact or overlap with each other.

70. A hair restoration treatment apparatus, wherein hair restoration treatment is conducted by irradiating a head with laser beams emitted from a semiconductor laser array apparatus, comprising:
- a first laser array structure which includes,
  - a plurality of first laser oscillation units which are arranged side by side at an interval, and
  - a first current blocking material which fills a space between each pair of adjacent first laser oscillation units; and,
- a second laser array structure which includes,
  - a plurality of second laser oscillation units which are arranged side by side at an interval, and
  - a second current blocking material which fills a space between each pair of adjacent second laser oscillation units,
- wherein, when the semiconductor laser array apparatus is activated, laser beams generated by the first laser array structure and the second laser array structure leak to the outside of the first and second laser array structures so as to form first and second distribution regions of the laser beams,
- and the first and second laser array structures are closely disposed so that the first and second distribution regions contact or overlap with each other.

71. A treatment apparatus for detached retinas, wherein treatment is conducted against detached retinas by irradiating retinas with laser beams emitted from a semiconductor laser array apparatus, comprising:
- a first laser array structure which includes,
  - a plurality of first laser oscillation units which are arranged side by side at an interval, and
  - a first current blocking material which fills a space between each pair of adjacent first laser oscillation units; and,
- a second laser array structure which includes,
  - a plurality of second laser oscillation units which are arranged side by side at an interval, and
  - a second current blocking material which fills a space between each pair of adjacent second laser oscillation units,
- wherein, when the semiconductor laser array apparatus is activated, laser beams generated by the first laser array structure and the second laser array structure leak to the outside of the first and second laser array structures so as to form first and second distribution regions of the laser beams,
- and the first and second laser array structures are closely disposed so that the first and second distribution regions contact or overlap with each other.

72. A treatment apparatus for myopia, wherein treatment is conducted against myopia by irradiating corneas with laser beams emitted from a semiconductor laser array apparatus, comprising:
- a first laser array structure which includes,
  - a plurality of first laser oscillation units which are arranged side by side at an interval, and
  - a first current blocking material which fills a space between each pair of adjacent first laser oscillation units; and,
- a second laser array structure which includes,
  - a plurality of second laser oscillation units which are arranged side by side at an interval, and
  - a second current blocking material which fills a space between each pair of adjacent second laser oscillation units,
- wherein, when the semiconductor laser array apparatus is activated, laser beams generated by the first laser array structure and the second laser array structure leak to the outside of the first and second laser array structures so as to form first and second distribution regions of the laser beams,
- and the first and second laser array structures are closely disposed so that the first and second distribution regions contact or overlap with each other.

73. A punching and cutting apparatus, wherein punching or cutting processing is performed by irradiating a target with laser beams emitted from a semiconductor laser array apparatus, comprising:
- a first laser array structure which includes,
  - a plurality of first laser oscillation units which are arranged side by side at an interval, and
  - a first current blocking material which fills a space between each pair of adjacent first laser oscillation units; and,
- a second laser array structure which includes,
  - a plurality of second laser oscillation units which are arranged side by side at an interval, and
  - a second current blocking material which fills a space between each pair of adjacent second laser oscillation units,
- wherein, when the semiconductor laser array apparatus is activated, laser beams generated by the first laser array structure and the second laser array structure leak to the outside of the first and second laser array structures so as to form first and second distribution regions of the laser beams,
- and the first and second laser array structures are closely disposed so that the first and second distribution regions contact or overlap with each other.

74. A surface treatment processing apparatus, wherein surface treatment processing is performed by irradiating a target with laser beams emitted from a semiconductor laser array apparatus, comprising:
- a first laser array structure which includes,
  - a plurality of first laser oscillation units which are arranged side by side at an interval, and
  - a first current blocking material which fills a space between each pair of adjacent first laser oscillation units; and,
- a second laser array structure which includes,
  - a plurality of second laser oscillation units which are arranged side by side at an interval, and
  - a second current blocking material which fills a space between each pair of adjacent second laser oscillation units,
- wherein, when the semiconductor laser array apparatus is activated, laser beams generated by the first laser array structure and the second laser array structure leak to the outside of the first and second laser array structures so as to form first and second distribution regions of the laser beams,
- and the first and second laser array structures are closely disposed so that the first and second distribution regions contact or overlap with each other.

* * * * *